US012799464B2

(12) United States Patent
Lee et al.

(10) Patent No.: US 12,799,464 B2
(45) Date of Patent: Nov. 17, 2026

(54) aroG ALDOLASE VARIANT AND METHOD FOR PRODUCING BRANCHED CHAIN AMINO ACIDS BY USING SAME

(71) Applicant: CJ CHEILJEDANG CORPORATION, Seoul (KR)

(72) Inventors: Hayun Lee, Seoul (KR); Ju Eun Kim, Seoul (KR); Ji Hye Lee, Seoul (KR); Heeseok Lee, Seoul (KR); Kyungrim Kim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 518 days.

(21) Appl. No.: 18/274,196

(22) PCT Filed: Nov. 18, 2021

(86) PCT No.: PCT/KR2021/016966

§ 371 (c)(1),
(2) Date: Jul. 25, 2023

(87) PCT Pub. No.: WO2022/163981

PCT Pub. Date: Aug. 4, 2022

(65) Prior Publication Data

US 2024/0093163 A1 Mar. 21, 2024

(30) Foreign Application Priority Data

Jan. 26, 2021 (KR) ........................ 10-2021-0010911

(51) Int. Cl.
*C12N 9/10* (2006.01)
*C12P 13/06* (2006.01)
*C12P 13/08* (2006.01)

(52) U.S. Cl.
CPC ............ *C12N 9/1085* (2013.01); *C12P 13/06* (2013.01); *C12P 13/08* (2013.01); *C12Y 205/01054* (2013.01)

(58) Field of Classification Search
None
See application file for complete search history.

(56) References Cited

U.S. PATENT DOCUMENTS

| | | | | |
|---|---|---|---|---|
| 7,355,029 | B2 * | 4/2008 | Zelder | C12N 9/00 536/23.7 |
| 7,662,943 | B2 | 2/2010 | Park et al. | |
| 8,178,322 | B2 | 5/2012 | Araki et al. | |
| 8,362,325 | B2 * | 1/2013 | Troukhan | C12Q 1/6895 800/278 |
| 8,465,962 | B2 | 6/2013 | Kim et al. | |
| 9,109,242 | B2 | 8/2015 | Park et al. | |
| 10,273,491 | B2 | 4/2019 | Lee et al. | |
| 10,584,338 | B2 | 3/2020 | Lee et al. | |
| 2020/0340022 | A1 | 10/2020 | Kwon et al. | |

FOREIGN PATENT DOCUMENTS

| | | | |
|---|---|---|---|
| EP | 2147972 | A1 | 1/2010 |
| JP | 3185261 | B2 | 7/2001 |
| JP | 3225597 | B2 | 11/2001 |
| KR | 10-2003-0048140 | A | 6/2003 |
| KR | 10-2007-0087091 | A | 8/2007 |
| KR | 10-2018-0077008 | A | 7/2018 |
| KR | 10-2143964 | B1 | 8/2020 |
| KR | 10-2020-0136813 | A | 12/2020 |

OTHER PUBLICATIONS

Singh et al. (Curr. Protein Pept. Sci. 18:1-11, 2017).*
Zhang et al. (Structure 26:1474-1485, 2018).*
Ngo et al. in The Protein Folding Problem and Tertiary Structure Prediction, 1994, Merz et al. (ed.), Birkhauser, Boston, MA, pp. 433 and 492-495.*
Franceus et al., J. Ind. Microbiol. Biotechnol. vol. 44, pp. 687-695, 2017.*
NCBI GenBank, "3-Deoxy-D-arabino-heptulosonate 7-phosphate (DAHP) synthase [Corynebacterium glutamicum K051]", GenBank: CCH25318.1, Feb. 27, 2015, 2 pages.
NCBI GenBank, "phospho-2-dehydro-3-deoxyheptonate aldolase [Corynebacterium callunae DSM 20147]", GenBank: AGG67274.1, Nov. 9, 2023, 2 pages.
NCBI GenBank, "Phospho-2-dehydro-3-deoxyheptonate aldolase 2, chloroplastic [Porphyridium purpureum]", GenBank: KAA8496087.1, Sep. 24, 2019, 2 pages.
NCBI GenBank, "Phospho-2-dehydro-3-deoxyheptonate aldolase [Paeniglutamicibacter gangotriensis Lz1 y]", GenBank: EMQ98133.1, Mar. 25, 2013, 2 pages.
NCBI GenBank, "3-deoxy-7-phosphoheptulonate synthase [Granulibacter bethesdensis CGDNIH1]", GenBank: ABI62318.1, Aug. 28, 2017, 2 pages.
NCBI GenBank, phospho-2-dehydro-3-deoxyheptonate aldolase [*Pseudomonas* sp. RtIB026]', GenBank: BCJ07696.1, Nov. 17, 2022, 2 pages.
NCBI GenBank, "3-deoxy-7-phosphoheptulonate synthase [Cyanidioschyzon merolae strain 10D]", GenBank: BAM83159.1, Mar. 19, 2019, 2 pages.
NCBI GenBank, "3-deoxy-7-phosphoheptulonate synthase [Emiliania huxleyi CCMP1516]", GenBank: EOD34161.1, Mar. 21, 2015, 2 pages.
NCBI GenBank, "3-deoxy-7-phosphoheptulonate synthase class II [*Streptomyces* sp. SID89]", GenBank: MYX43123.1, Jan. 13, 2020, 2 pages.

(Continued)

*Primary Examiner* — Richard G Hutson

(74) *Attorney, Agent, or Firm* — Morgan, Lewis & Bockius LLP

(57) ABSTRACT

The present application relates to an aroG aldolase (phospho-2-dehydro-3-deoxyheptonate aldolase) variant, a microorganism comprising the same, and a method for producing amino acids using the same.

20 Claims, No Drawings

Specification includes a Sequence Listing.

(56) References Cited

OTHER PUBLICATIONS

NCBI GenBank, "phospho-2-dehydro-3-deoxyheptonate aldolase [Beutenbergia cavernae DSM 12333]", GenBank: ACQ80162.1, Jan. 28, 2014, 2 pages.

NCBI GenBank, "MAG TPA: 3-deoxy-7-phosphoheptulonate synthase class II [Rhodospirillaceae bacterium]", GenBank: HAX92203.1, Sep. 6, 2018, 2 pages.

NCBI GenBank, "Phospho-2-dehydro-3-deoxyheptonate aldolase [Rhodopseudomonas palustris]", GenBank: QQM03493.1, Apr. 15, 2021.

NCBI GenBank, "phospho-2-dehydro-3-deoxyheptonate aldolase AroH [Gordonia polyisoprenivorans VH2]", GenBank: AFA73815.1, Jan. 16, 2015, 2 pages.

NCBI GenBank, "phospho-2-dehydro-3-deoxyheptonate aldolase [Hoyosella rhizosphaerae]", GenBank: GGC71130.1, Aug. 26, 2023, 2 pages.

NCBI GenBank, "MAG: 3-deoxy-7-phosphoheptulonate synthase class II [Acidimicrobiales bacterium]", GenBank: PZS11495.1, Jun. 18, 2018, 2 pages.

NCBI GenBank, "3-deoxy-7-phosphoheptulonate synthase class II [Ornithinimicrobium ciconiae]", GenBank: 0D088412.1, Nov. 12, 2021, 2 pages.

NCBI GenBank, "phospho-2-dehydro-3-deoxyheptonate aldolase [*Streptomyces* sp. PBH53]", GenBank: AKN72332.1, Aug. 5, 2015, 2 pages.

Liu et al., "Integration of *E.coli* aroG-pheA tandem genes into Corynebacterium glutamicum tyrA locus and its effect on L-phenylalanine biosynthesis", World J Gastroenterol, vol. 10, No. 24, 2004, pp. 3683-3687.

Office Action issued in corresponding Australian Patent Application No. 2021423180, dated Feb. 4, 2025.

Extended European Search Report issued in the corresponding Application No. 21923390.5, mailed May 24, 2024.

Lin et al., "Site-directed mutagenesis and over expression of aroG gene of *Escherichia coli* K-12", International Journal of Biological Macromolecules, vol. 51, No. 5, Dec. 1, 2012, pp. 915-919, XP002769347.

NCBI, Genbank accession No. WP_011014936.1; 3-deoxy-7-phosphoheptulonate synthase class II [Corynebacterium glutamicum] (Dec. 16, 2020).

Needleman et al., "A General Method Applicable to the Search for Similarities in the Amino Acid Sequence of Two Proteins," J. Mol. Biol., 48: 443-453 (1970).

International Search Report issued in corresponding International Patent Application No. PCT/KR2021/016966 dated Mar. 8, 2022.

* cited by examiner aroG ALDOLASE VARIANT AND METHOD FOR PRODUCING BRANCHED CHAIN AMINO ACIDS BY USING SAME A computer readable text file, entitled "133660-04-9001-US_Sequence_Listing.txt," created on or about Aug. 14, 2023, with a file size of 74,905 bytes contains the sequence listing for this application and is hereby incorporated by reference in its entirety.

TECHNICAL FIELD

The present application relates to an aroG aldolase (phospho-2-dehydro-3-deoxyheptonate aldolase) variant, and a method for producing amino acids using the same.

BACKGROUND ART

L-Amino acids are the basic building blocks of proteins and are used as important materials for pharmaceutical raw materials, food additives, animal feeds, nutritional supplements, pesticides, bactericides, etc. Therefore, the industrial production of amino acids has become an important industrial process from an economic perspective.

Various studies have been conducted for efficiently producing amino acids; for example, efforts have been made to develop microorganisms or fermentation process technologies for producing amino acids with high efficiency. In particular, specific approaches to target materials have been developed, such as enhancement of expression of genes encoding enzymes involved in the biosynthesis of amino acids in the strains of the genus *Corynebacterium* or deletion of genes unnecessary for the biosynthesis of amino acids (U.S. Pat. No. 9,109,242 B2). In addition to these methods, a method for removing genes that are not involved in the production of amino acids and a method for removing genes whose functions for producing amino acids are not specifically known has also been utilized.

Meanwhile, among the amino acids, branched-chain amino acids refer to the three amino acids valine, leucine, and isoleucine, and it is known that they are mainly metabolized in muscle tissue and serve as an energy source during exercise. As branched-chain amino acids are known to play an important role in muscle maintenance and growth during exercise, use thereof is increasing. However, since a large amount of by-products are generated in the biosynthesis pathway of branched-chain amino acids, it is important to reduce the amount of by-products in order to produce branched-chain amino acids in a high yield and with high purity.

DISCLOSURE

Technical Problem

The present inventors have confirmed that a microorganism into which the newly developed aroG aldolase variant has been introduced can produce branched-chain amino acids in a high yield and with high purity, thereby completing the present application.

Technical Solution

It is one object of the present application to provide an aroG aldolase (phospho-2-dehydro-3-deoxyheptonate aldolase) variant, in which any one or more amino acids corresponding to positions 217, 310, 403, and 462 from the N-terminus in the amino acid sequence of SEQ ID NO: 1 is substituted with another amino acid.

It is another object of the present application to provide a polynucleotide encoding the variant and a vector containing the same.

It is still another object of the present application to provide a microorganism of the genus *Corynebacterium*, including one or more of the aroG aldolase variant, the polynucleotide, and the vector.

It is yet another object of the present application to provide a method for producing branched-chain amino acids, including culturing the microorganism in a medium.

Advantageous Effects

When the aroG aldolase variant of the present application is used, the production of by-products can be reduced, and branched-chain amino acids can be produced in a high yield compared to the case where the aroG aldolase variant is not used.

DETAILED DESCRIPTION OF PREFERRED EMBODIMENTS

The present application will be described in detail as follows. Meanwhile, each description and embodiment disclosed herein can be applied to other descriptions and embodiments, respectively. That is, all combinations of various elements disclosed herein fall within the scope of the present application. Further, the scope of the present application is not limited by the specific description described below.

Additionally, those of ordinary skill in the art may be able to recognize or confirm, using only conventional experimentation, many equivalents to the particular aspects of the invention described herein. Furthermore, it is also intended that these equivalents be included in the present application.

One aspect of the present application provides an aroG aldolase (phospho-2-dehydro-3-deoxyheptonate aldolase) variant, in which any one or more amino acids corresponding to positions 217, 310, 403, and 462 from the N-terminus in the amino acid sequence of SEQ ID NO: 1 is substituted with another amino acid.

The aroG aldolase variant refers to a variant in which any one or more amino acids corresponding to positions 217, 310, 403, and 462 from the N-terminus in the amino acid sequence of SEQ ID NO: 1 is substituted with another amino acid, in a polypeptide having the aroG aldolase activity or in the aroG aldolase.

As used herein, the term "aroG aldolase" is an enzyme that is able to catalyze the following reaction:

Phosphoenolpyruvate+D-erythrose 4-phosphate+$H_2O$↔3-deoxy-D-arabino-hept-2-ulosonate 7-phosphate+phosphate The aroG aldolase of the present application may be an aroG aldolase to which modifications are applied to prepare the aroG aldolase variant provided herein, or a polypeptide having the aroG aldolase activity. Specifically, it may be a naturally occurring polypeptide or a wild-type polypeptide, may be a mature polypeptide thereof, and may include a variant or a functional fragment thereof without limitation as long as it can be a parent of the aroG aldolase variant of the present application.

As used herein, the aroG aldolase may be a polypeptide of SEQ ID NO: 1, but is not limited thereto. In one embodiment, it may be a polypeptide having a sequence identity of about 60%, 70%, 75%. 80%. 85%, 90%, 95%, 96%, 97%, 98%, or 99% or more with the polypeptide of SEQ ID NO: 1, and any polypeptide having an activity identical or corresponding to the polypeptide consisting of the amino acid sequence of SEQ ID NO: 1 may be included within the scope of the aroG aldolase, without limitation.

The sequence of the aroG aldolase of the present application can be obtained from GenBank of NCBI, a known database. Specifically, it may be a polypeptide encoded by the aroG gene, but is not limited thereto.

As used herein, the "variant" refers to a polypeptide having one or more amino acids different from the amino acid sequence before modification of the variant by conservative substitutions and/or modifications such that the functions and properties of the polypeptide are retained. Such variants may generally be identified by modifying one or more of the above amino acid sequences of the polypeptide and evaluating the properties of the modified polypeptide. That is, the ability of the variants may be enhanced, unchanged, or diminished relative to a polypeptide before modification. Further, some variants may include those in which one or more portions, such as an N-terminal leader sequence or transmembrane domain, have been removed. Other variants may include those in which a portion has been removed from the N- and/or C-terminus of a mature protein. The term "variant" may be used interchangeably with terms such as modified, modification, modified polypeptide, modified protein, mutation and mutant, etc. without limitation, as long as the terms are used to indicate variation.

Additionally, the variants may also include deletion or addition of amino acids that have minimal influence on the properties and secondary structure of the polypeptide. For example, a signal (or leader) sequence involved in the translocation of proteins may be conjugated at the N-terminus of the variant co-translationally or post-translationally. Further, the variants may also be conjugated with another sequence or linker to identify, purify, or synthesize the polypeptide.

The variant provided herein may be an aroG aldolase variant in which any one or more amino acids corresponding to positions 217, 310, 403, and 462 from the N-terminus in the amino acid sequence of SEQ ID NO: 1 is substituted with another amino acid. For example, in the above positions, 2 or more, 3 or more, or all of 4 amino acids may be substituted, but is not limited thereto.

The amino acid corresponding to position 217 from the N-terminus in the amino acid sequence of SEQ ID NO: 1 may be arginine; the amino acid corresponding to position 310 may be lysine; the amino acid corresponding to position 403 may be arginine; and/or the amino acid corresponding to position 462 may be glutamic acid.

The variant provided herein may include one or more substitutions from: a substitution of an amino acid corresponding to position 217 from the N-terminus in the amino acid sequence of SEQ ID NO: 1 with an amino acid except arginine; a substitution of an amino acid corresponding to position 310 with an amino acid except lysine; a substitution of an amino acid corresponding to position 403 with an amino acid except arginine; and a substitution of an amino acid corresponding to position 462 with an amino acid except glutamic acid, but is not limited thereto.

The term "another amino acid" is not limited as long as it is an amino acid different from the amino acid before substitution. Meanwhile, when it is expressed that "a specific amino acid has been substituted", it is obvious that the amino acid is substituted with an amino acid different from the amino acid before substitution, even if it is not specifically stated that the amino acid has been substituted with a different amino acid.

In one embodiment, the variant of the present application may be those in which any one or more amino acids corresponding to positions 217, 310, 403, and 462 in the amino acid sequence of SEQ ID NO: 1, which is the reference protein, is substituted with a hydrophobic amino acid or an aliphatic amino acid, which is different from the amino acid before substitution.

Specifically, the variant may be those in which any one or more amino acids corresponding to positions 217, 310, 403, and 462 in the amino acid sequence of SEQ ID NO: 1 is substituted with a hydrophobic (nonpolar) amino acid or an aliphatic amino acid. The aliphatic amino acid may be, for example, an amino acid selected from the group consisting of glycine, alanine, valine, leucine, and isoleucine, but is not limited thereto. The hydrophobic (nonpolar) amino acid may be, for example, an amino acid selected from the group consisting of glycine, methionine, alanine, valine, leucine, isoleucine, proline, phenylalanine, tyrosine, and tryptophan, but is not limited thereto.

In one embodiment, the variant of the present application may be those in which any one or more amino acids corresponding to positions 217, 310, 403, and 462 in the amino acid sequence of SEQ ID NO: 1 with an amino acid different from the amino acid before substitution, among small-sized amino acids, but is not limited thereto.

As used herein, the term "small-sized amino acid" may include amino acids with a relatively small size among the 20 amino acids, such as glycine, alanine, serine, threonine, cysteine, valine, leucine, isoleucine, proline, and asparagine, and may specifically refer to glycine, alanine, serine, threonine, cysteine, valine, leucine, isoleucine, and proline, but is not limited thereto. More specifically, it may refer to glycine, alanine, valine, leucine, isoleucine, serine, and threonine, but is not limited thereto.

More specifically, the substitution with another amino acid with respect to the variant of the present application may be a substitution with alanine, but is not limited thereto.

As used herein, the term "corresponding to" refers to an amino acid residue at a position listed in a polypeptide, or an amino acid residue similar to, identical to, or homologous to a residue listed in a polypeptide. Identifying an amino acid at a corresponding position may be to determine a specific amino acid in a sequence that refers to a specific sequence. As used herein, the term "corresponding region" generally refers to a similar or corresponding position in a related protein or reference protein.

For example, any amino acid sequence is aligned with SEQ ID NO: 1, and based on the alignment, each amino acid residue of the amino acid sequence can be numbered with reference to the numerical position of the amino acid residue corresponding to the amino acid residue of SEQ ID NO: 1. For example, a sequence alignment algorithm such as that described herein can identify the position of an amino acid or a position where modifications such as substitutions, insertions or deletions occur compared to a query sequence (also referred to as a "reference sequence").

Example of the alignment may be determined by the Needleman-Wunsch algorithm (Needleman and Wunsch, 1970, J. Mol. Biol. 48:443-453), which is performed using the Needleman program of the EMBOSS package (EMBOSS: The European Molecular Biology Open Software Suite, Rice et al., 2000, *Trends Genet.* 16:276-277), etc., but is not limited thereto, and sequence alignment programs, such as pairwise sequence comparison algorithms, etc., known in the art may be appropriately used.

In one embodiment, the variant of the present application may be those, in which any one or more amino acids corresponding to positions 217, 310, 403, and 462 in the amino acid sequence of SEQ ID NO: 1 is substituted with another amino acid, while having a sequence identity of about 60%, 70%, 75%. 80%. 85%, 90%, 95%, 96%, 97%, 98%, or 99% or more with the polypeptide of SEQ ID NO: 1.

In one embodiment, the variant of the present application may include an amino acid sequence having a homology or identity of at least 70%, 75%, 80%, 85%, 90%, 95%, 96%, 97%, 98%, 99%, 99.5%, 99.7%, or 99.9% with the amino acid sequence represented by SEQ ID NO: 3, SEQ ID NO: 5, SEQ ID NO: 7, SEQ ID NO: 9, SEQ ID NO: 23, or SEQ ID NO: 25.

Specifically, the variant of the present application may have, include, consist of or consist essentially of the amino acid sequence represented by SEQ ID NO: 3, SEQ ID NO: 5, SEQ ID NO: 7, SEQ ID NO: 9, SEQ ID NO: 23, or SEQ ID NO: 25.

In one embodiment, the variant of the present application may include an amino acid sequence in which any one or more amino acid corresponding to the positions 217, 310, 403, and 462 is alanine based on the amino acid sequence of SEQ ID NO: 1 and which has a homology or identity of at least 70%, 75%, 80%, 85%, 90%, 95%, 96%, 97%, 98%, 99%, 99.5%, 99.7%, or 99.9% with the amino acid sequence represented by SEQ ID NO: 3, SEQ ID NO: 5, SEQ ID NO: 7, SEQ ID NO: 9, SEQ ID NO: 23, or SEQ ID NO: 25. Additionally, it is apparent that variants having an amino acid sequence, in which a part of the amino acid sequence is deleted, modified, substituted, conservatively substituted or added, may fall within the scope of the present application, as long as the amino add sequence has such homology or identity and shows an efficacy corresponding to that of the variant of the present application.

For example, it may include sequence additions or deletions, naturally occurring mutations, silent mutations or conservative substitutions that do not alter the function of the variant of the present application at the N-terminus, at the C-terminus, and/or within the amino acid sequence.

As used herein, the term "conservative substitution" refers to substitution of an amino acid with another amino acid having similar structural and/or chemical properties. Such amino acid substitution may generally occur based on similarity of polarity, charge, solubility, hydrophobicity, hydrophilicity, and/or amphipathic nature of a residue. Typically, conservative substitutions may have little or no effect on the activity of a protein or polypeptide.

As used herein, the term "homology" or "identity" refers to a degree of relatedness between two given amino acid sequences or nucleotide sequences, and may be expressed as a percentage. The terms homology and identity may often be used interchangeably with each other.

The sequence homology or identity of conserved polypeptide or polynucleotide sequences may be determined by standard alignment algorithms and can be used with a default gap penalty established by the program being used. Substantially, homologous or identical sequences are generally expected to hybridize to all or part of the entire length of the sequences under moderate or high stringent conditions. It is apparent that polynucleotides that contain degenerate codons instead of codons in hybridizing polynucleotides are also considered.

Whether any two polynucleotide sequences have a homology, similarity or identity may be, for example, determined by a known computer algorithm such as the "FASTA" program using default parameters (Pearson et al., (1988) *Proc. Natl. Acad. Sci. USA* 85:2444). Alternatively, it may be determined by the Needleman—Wunsch algorithm (Needleman and Wunsch, 1970, *J. Mol. Biol.* 48:443-453), which is performed using the Needleman program of the EMBOSS package (EMBOSS:The European Molecular Biology Open Software Suite, Rice et al., 2000, *Trends Genet.* 16:276-277) (version 5.0.0 or later) (GCG program package (Devereux, J., et al., *Nucleic Acids Research* 12:387 (1984)), BLASTP, BLASTN, FASTA (Atschul, S. F., et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, the homology, similarity or identity may be determined using BLAST or ClustalW of the National Center for Biotechnology Information (NCB).

The homology, similarity or identity of polypeptides or polynucleotides may be determined by comparing sequence information using, for example, the GAP computer program, such as Needleman et al. (1970), *J Mol Biol.* 48:443 as disclosed in Smith and Waterman, *Adv. Appl. Math* (1981) 2:482. In summary, the GAP program defines the homology, similarity or identity as the value obtained by dividing the number of similarly aligned symbols (i.e., nucleotides or amino acids) by the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), *Nucl. Acids Res.* 14:6745, as disclosed in Schwartz and Dayhoff, eds., *Atlas of Protein Sequence and Structure*, National Biomedical Research Foundation, pp. 353-358 (1979) (or EDNAFULL substitution matrix (EMBOSS version of NCBI NUC4.4)); (2) a penalty of 3.0 for each gap and an additional 0.10 penalty for each symbol in each gap (or a gap opening penalty of 10 and a gap extension penalty of 0.5); and (3) no penalty for end gaps.

In one embodiment, the variant of the present application may have the aroG aldolase activity. In one embodiment, the variant of the present application may have an activity capable of increasing the production ability of branched-chain amino acids compared to a wild-type or non-modified aroG aldolase. In one embodiment, the variant of the present application may have an activity capable of decreasing the production level of by-products in the production pathway of branched-chain amino acids, compared to a wild-type or non-modified aroG aldolase. In one embodiment, the variant of the present application may have a weakened activity compared to a wild-type or non-modified aroG aldolase, but is not limited thereto.

Another aspect of the present application provides a polynucleotide encoding the variant of the present application.

As used herein, the "polynucleotide", which is a polymer of nucleotides composed of nucleotide monomers connected in a lengthy chain by a covalently bond, is a DNA or RNA strand having at least a certain length. More specifically, it may refer to a polynucleotide fragment encoding the variant.

The polynucleotide encoding the variant of the present application may include a nucleotide sequence encoding the amino acid sequence represented by SEQ ID NO: 3, SEQ ID NO: 5, SEQ ID NO: 7, SEQ ID NO: 9, SEQ ID NO: 23, or SEQ ID NO: 25. As an example of the present application, the polynucleotide of the present application may have or include the sequence of SEQ ID NO: 4, SEQ ID NO: 6, SEQ ID NO: 8, SEQ ID NO: 10, SEQ ID NO: 24, or SEQ ID NO: 26. In addition, the polynucleotide of the present application may consist of or consist essentially of the sequence of SEQ ID NO: 4, SEQ ID NO: 6, SEQ ID NO: 8, SEQ ID NO: 10, SEQ ID NO: 24, or SEQ ID NO: 26.

The polynucleotide of the present application may undergo various modifications in the coding region within the scope that does not change the amino acid sequence of the variant of the present application, due to codon degeneracy or in consideration of the codons preferred in an organism in which the variant of the present application is to be expressed. Specifically, the polynucleotide of the present application may have or include a nucleotide sequence having a homology or identity of 70% or more, 75% or more, 80% or more, 85% or more, 90% or more, 95% or more, 96% or more, 97% or more, 98% or more, and 100% or less with the sequence of SEQ ID NO: 4, SEQ ID NO: 6, SEQ ID NO: 8, SEQ ID NO: 10, SEQ ID NO: 24, or SEQ ID NO: 26, or may consist of or consist essentially of a nucleotide sequence having a homology or identity of 70% or more, 75% or more, 80% or more, 85% or more, 90% or more, 95% or more, 96% or more, 97% or more, 98% or more, and 100% or less with the sequence of SEQ ID NO: 4, SEQ ID NO: 6, SEQ ID NO: 8, SEQ ID NO: 10, SEQ ID NO: 24, or SEQ ID NO: 26, but is not limited thereto.

In particular, in the sequence having the homology or identity, codons encoding the amino acids corresponding to positions 217, 310, 403, and 462 of SEQ ID NO: 4, SEQ ID NO: 6, SEQ ID NO: 8, SEQ ID NO: 10, SEQ ID NO: 24, or SEQ ID NO: 26 may be one of the codons encoding alanine.

Additionally, the polynucleotide of the present application may include a probe that may be prepared from a known gene sequence, for example, any sequence which can hybridize with a sequence complementary to all or part of the polynucleotide sequence of the present application under stringent without limitation. The "stringent conditions" refers to conditions under which specific hybridization between polynucleotides is allowed. Such conditions are specifically described in the literature (J. Sambrook et al., *Molecular Cloning, A Laboratory Manual,* 2nd Edition, Cold Spring Harbor Laboratory press, Cold Spring Harbor, New York, 1989; F. M. Ausubel et al., *Current Protocols in Molecular Biology*, John Wiley & Sons, Inc., New York, 9.50-9.51, 11.7-11.8). For example, the stringent conditions may include conditions under which genes having a high homology or identity of 70% or more, 75% or more, 80% or more, 85% or more, 90% or more, 95% or more, 96% or more, 97% or more, 98% or more, or 99% or more are hybridized with each other and genes having a homology or identity lower than the above homologies or identities are not hybridized with each other, or washing conditions of Southern hybridization, that is, washing once, specifically, twice or three times at a salt concentration and a temperature corresponding to 60° C., 1×SSC, 0.1% SDS, specifically 60° C., 0.1×SSC, 0.1% SDS, and more specifically 68° C., 0.1×SSC, 0.1% SDS.

Hybridization requires that two nucleic acids contain complementary sequences, although mismatches between bases are possible depending on the stringency of the hybridization. The term "complementary" is used to describe the relationship between nucleotide bases that can hybridize with each other. For example, with respect to DNA, adenosine is complementary to thymine, and cytosine is complementary to guanine. Therefore, the polynucleotide of the present application may include isolated nucleotide fragments complementary to the entire sequence as well as nucleic acid sequences substantially similar thereto.

Specifically, polynucleotides having a homology or identity with the polynucleotide of the present application may be detected using the hybridization conditions including a hybridization step at a $T_m$ value of 55° C. under the above-described conditions. Further, the $T_m$ value may be 60° C., 63° C., or 65° C., but is not limited thereto, and may be appropriately adjusted by those skilled in the art depending on the purpose thereof.

The appropriate stringency for hybridizing the polynucleotides depends on the length of the polynucleotides and the degree of complementation, and these variables are well known in the art (e.g., Sambrook et al.).

Still another aspect of the present application provides a vector containing the polynucleotide of the present application. The vector may be an expression vector for expressing the polynucleotide in a host cell, but is not limited thereto.

As used herein, the term "vector" refers to a DNA construct containing the nucleotide sequence of a polynucleotide encoding the target polypeptide operably linked to a suitable expression regulatory region (expression regulatory sequence) so as to be able to express the target polypeptide in a suitable host cell. The expression regulatory sequence may include a promoter capable of initiating transcription, any operator sequence for regulating the transcription, a sequence encoding a suitable mRNA ribosome-binding site, and a sequence for regulating termination of transcription and translation. Once transformed into a suitable host cell, the vector may replicate or function independently from the host genome, or may integrate into genome thereof.

The vector used in the present application is not particularly limited, and any vector known in the art may be used. Examples of the vector typically used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, and Charon21A, etc. may be used; and as a plasmid vector, those based on pDC, pBR, pUC, pBluescriptll, pGEM, pTZ, pCL, pET, etc. may be used. Specifically, pDC, pDCM2, pACYC177, pACYC184, pCL, pECCG117, pUC19, pBR322, pMW118, and pCC1 BAC vector may be used.

In one example, a polynucleotide encoding a target polypeptide may be inserted into the chromosome through a vector for intracellular chromosomal insertion. The insertion of the polynucleotide into the chromosome may be performed by any method known in the art, for example, by homologous recombination, but is not limited thereto. The vector may further include a selection marker to confirm the insertion into the chromosome. The selection marker is for selecting the cells transformed with the vector, that is, for confirming whether the target nucleic acid molecule has been inserted, and markers that provide selectable phenotypes, such as drug resistance, auxotrophy, resistance to cell toxic agents, or expression of surface proteins, may be used. Only cells expressing the selection marker are able to survive or to show different phenotypes under the environment treated with the selective agent, and thus the transformed cells may be selected.

As used herein, the term "transformation" refers to the introduction of a vector containing a polynucleotide encoding a target polypeptide into a host cell or a microorganism so that the polypeptide encoded by the polynucleotide can be expressed in the host cell. As long as the transformed polynucleotide can be expressed in the host cell, it does not matter whether the transformed polynucleotide is integrated into the chromosome of the host cell and located therein or located extrachromosomally, and both cases can be included. Further, the polynucleotide may include DNA and RNA encoding the target polypeptide. The polynucleotide may be introduced in any form, as long as it can be introduced into the host cell and expressed therein. For example, the polynucleotide may be introduced into the host cell in the form of an expression cassette, which is a gene construct including all elements required for its autonomous expression. The expression cassette may commonly include a promoter operably linked to the polynucleotide, a transcription terminator, a ribosome-binding site, or a translation terminator. The expression cassette may be in the form of a self-replicable expression vector. Additionally, the polynucleotide may be introduced into the host cell as it is and operably linked to sequences required for expression in the host cell, but is not limited thereto.

Further, as used herein, the term "operably linked" means that the polynucleotide sequence is functionally linked to a promoter sequence that initiates and mediates transcription of the polynucleotide encoding the target variant of the present application.

Yet another aspect of the present application provides a microorganism of the genus *Corynebacterium*, including one or more of the variant of the present application, the polynucleotide of the present application and the vector of the present application.

The microorganism may include the variant polypeptide of the present application, a polynucleotide encoding the polypeptide, or a vector containing the polynucleotide of the present application.

As used herein, the term "microorganism" or "strain" includes all wild-type microorganisms, or naturally or artificially genetically modified microorganisms, and it may be a microorganism in which a particular mechanism is weakened or enhanced due to insertion of a foreign gene, or enhancement or inactivation of the activity of an endogenous gene, and may be a microorganism including genetic modification to produce a desired polypeptide, protein or product.

The strain of the present application may be a strain including any one or more of the variant of the present application, the polynucleotide of the present application, and a vector containing the polynucleotide of the present application; a strain modified to express the variant of the present application or the polynucleotide of the present application; a strain expressing the variant of the present application or the polynucleotide of the present application (e.g., a recombinant strain); or a strain having the activity of the variant of the present application (e.g., a recombinant strain), but is not limited thereto.

The strain of the present application may be a strain having the production ability of branched-chain amino acids.

The strain of the present application is a microorganism having the ability to naturally produce aroG aldolase or branched-chain amino acids, or a microorganism in which the variant of the present application or a polynucleotide encoding the same (or a vector containing the polynucleotide) has been introduced into the aroG aldolase or the parent strain having no ability to produce branched-chain amino acids and/or in which the ability to produce branched-chain amino acid productivity has been imparted, but is not limited thereto.

In one example, the strain of the present application strain is a cell or microorganism which is transformed with a vector containing the polynucleotide of the present application or a polynucleotide encoding the variant of the present application to express the variant of the present application, and for the purpose of the present application, the strain may include all microorganisms capable of producing branched-chain amino acids, including the variant of the present application. For example, the strain of the present application may be a recombinant strain in which the production ability of branched-chain amino acids has been increased upon expression of the aroG aldolase variant by introducing the polynucleotide encoding the variant of the present application into a natural wild-type microorganism or a microorganism for producing branched-chain amino acids. The recombinant strain in which the production ability of branched-chain amino acids is increased may be a microorganism in which the production ability of branched-chain amino acids has been increased compared to that of a natural wild-type microorganism or aroG aldolase non-modified microorganism (that is, a microorganism expressing a wild-type aroG aldolase), but is not limited thereto.

In one example, the aroG aldolase non-modified microorganism, the target strain to be compared to determine the increase in the production ability of branched-chain amino acids, may be a *Corynebacterium glutamicum* ATCC13032 strain. In another example, the aroG aldolase non-modified microorganism, the target strain to be compared to determine the increase in the production ability of branched-chain amino acids, may be CJL-8109, KCCM12739P (CA10-3101), or KCCM11201P, but is not limited thereto.

In one example, the recombinant strain may have an increased production ability of branched-chain amino acids by about 1% or more, specifically, about 3% or about 5%, compared to the parent strain before modification or a non-modified microorganism, but is not limited thereto, as long as it has an increased+value compared to the production ability of the parent strain before modification or a non-modified microorganism.

In another example, the recombinant strain may have a decreased production of by-products generated in the production pathway of branched-chain amino acids by about 50% or less, specifically, about 30% or less or about 10% or less, compared to the parent strain before modification or a non-modified microorganism, but is not limited thereto.

As used herein, the term "about" refers to a range including all of ±0.5, ±0.4, ±0.3, ±0.2, ±0.1, etc., and it includes all of the values equivalent to those which come immediately after the term "above" or those in a similar range, but is not limited thereto.

As used herein, the term "branched-chain amino acid" refers to an amino acid having a branched alkyl group in the side chain, and includes valine, leucine and isoleucine. Specifically, in the present application, the branched-chain amino acid may be an L-branched-chain amino acid, and the L-branched-chain amino acid may be one or more selected from L-valine, L-leucine and L-isoleucine, but is limited thereto.

In the present application, the by-products generated in the production pathway of branched-chain amino acids refer to substances other than branched-chain amino acids, and specifically, aromatic amino acids, and more specifically, one or more selected from L-tyrosine and L-phenylalanine, but is not limited thereto.

As used herein, the term "non-modified microorganism" does not exclude a strain containing a mutation that may occur naturally in a microorganism, and may refer to a wild-type strain or a natural-type strain itself, or a strain before the trait is altered due to genetic modification caused by natural or artificial factors. For example, the non-modified microorganism may refer to a strain in which the aroG aldolase variant of the present application has not been introduced or a strain before introduction thereof. The "non-modified microorganism" may be used interchangeably with "strain before modification", "microorganism before modification", "non-mutant strain", "non-modified strain", "non-mutant microorganism", or "reference microorganism".

In one embodiment, the microorganism of the present application may be *Corynebacterium stationis, Corynebacterium* crudilactis, *Corynebacterium deserti, Corynebacterium efficiens, Corynebacterium callunae, Corynebacterium glutamicum, Corynebacterium singulare, Corynebacterium halotolerans, Corynebacterium striatum, Corynebacterium ammoniagenes, Corynebacterium pollutisoli, Corynebacterium imitans, Corynebacterium testudinoris*, or *Corynebacterium flavescens.*

The microorganism of the present application may further include a modification to increase the production ability of the branched-chain amino acids.

In one embodiment, the microorganism of the present application may include alternation in activity of one or more of isopropylmalate synthase, homoserine dehydrogenase, threonine dehydratase, branched-chain amino acid aminotransferase and citrate synthase.

In one embodiment, the microorganism of the present application may be a microorganism in which the activity of one or more of isopropylmalate synthase, branched-chain amino acid aminotransferase, homoserine dehydrogenase and threonine dehydratase is further enhanced.

In one embodiment, the microorganism of the present application may be a microorganism in which the activity of citrate synthase is further weakened.

However, the present application is not limited to the above-described description, and those skilled in the art may appropriately select additional modifications included in the microorganism according to the branched-chain amino acids to be produced.

As used herein, the "enhancement" of a polypeptide activity means that the activity of a polypeptide is increased compared to its endogenous activity. The enhancement may be used interchangeably with terms such as activation, up-regulation, overexpression, increase, etc. In particular, the terms activation, enhancement, up-regulation, overexpression and increase may include both cases in which an activity not originally possessed is exhibited, or the activity is enhanced compared to the endogenous activity or the activity before modification. The "endogenous activity" refers to the activity of a specific polypeptide originally possessed by a parental strain or a non-modified microorganism prior to transformation thereof, when the traits of the microorganism are altered through genetic modification due to natural or artificial factors, and may be used interchangeably with "activity before modification". The "enhancement", "up-regulation", "overexpression", or "increase" in the activity of a polypeptide compared to its endogenous activity means that the activity and/or concentration (expression level) is improved compared to that of a specific polypeptide originally possessed by a parent strain or a non-modified microorganism prior to transformation.

The enhancement may be achieved by introducing a foreign polypeptide, or by enhancing the activity and/or concentration (expression level) of the endogenous polypeptide. The enhancement of the activity of the polypeptide can be confirmed by the increase in the level of activity of the polypeptide, expression level, or the amount of product excreted from the polypeptide.

The enhancement of the activity of the polypeptide can be applied by various methods well known in the art, and is not limited as long as it can enhance the activity of the target polypeptide compared to that of the microorganism before modification. Specifically, genetic engineering and/or protein engineering well known to those skilled in the art, which is a common method of molecular biology, may be used, but the method is not limited thereto (e.g., Sitnicka et al. Functional Analysis of Genes. Advances in Cell Biology. 2010, Vol. 2. 1-16, Sambrook et al. *Molecular Cloning* 2012, etc.).

Specifically, the enhancement of the polypeptide of the present application may be achieved by:

1) increasing the intracellular copy number of a polynucleotide encoding the polypeptide;
2) replacing the expression regulatory region of a gene encoding the polypeptide on a chromosome with a sequence having a strong activity;
3) modifying the nucleotide sequence encoding the initiation codon or 5'-UTR of a gene transcript encoding the polypeptide;
4) modifying the amino acid sequence of the polypeptide such that the activity of the polypeptide is enhanced;
5) modifying the polynucleotide sequence encoding the polypeptide such that the activity of the polypeptide is enhanced (e.g., modifying the polynucleotide sequence of the polypeptide gene to encode a polypeptide that has been modified to enhance the activity of the polypeptide;
6) introducing a foreign polynucleotide having the activity of the polypeptide or a foreign polynucleotide encoding the same;
7) codon-optimization of a polynucleotide encoding the polypeptide;
8) analyzing the tertiary structure of the polypeptide and thereby selecting and modifying the exposed site, or chemically modifying the same; or
9) a combination of two or more selected from above 1 to 8), but is not limited thereto.

More specifically,

The 1) method of increasing the intracellular copy number of a gene encoding the polypeptide may be achieved by introducing a vector, which is operably linked to a polynucleotide encoding the polypeptide and is able to replicate and function regardless of a host cell, into the host cell. Alternatively, the method may be achieved by introducing one copy or two copies of polynucleotides encoding the polypeptide into the chromosome of a host cell. The introduction into the chromosome may be performed by introducing a vector, which is able to insert the polynucleotide into the chromosome of a host cell, into the host cell, but is not limited thereto. The vector is the same as described above.

The 2) method of replacing the expression regulatory region (or expression regulatory sequence) of a gene encoding the polypeptide on a chromosome with a sequence having a strong activity may be achieved by inducing a modification on the sequence through deletion, insertion, non-conservative or conservative substitution, or a combination thereof to further enhance the activity of the expression regulatory region, or by replacing the sequence with a sequence having a stronger activity. The expression regulatory region may include, but is not particularly limited to, a promoter, an operator sequence, a sequence encoding a ribosome-binding site, and a sequence regulating the termination of transcription and translation. In one example, the method may include replacing the original promoter with a strong promoter, but is not limited thereto.

Examples of the strong promoter may include cj1 to cj7 promoters (U.S. Pat. No. 7,662,943 B2), lac promoter, trp promoter, trc promoter, tac promoter, lambda phage PR promoter, PL promoter, tet promoter, gapA promoter, SPL7 promoter, SPL13(sm3) promoter (U.S. Ser. No. 10/584,338 B2), 02 promoter (U.S. Ser. No. 10/273,491 B2), tkt promoter, yccA promoter, etc., but is not limited thereto.

The 3) method of modifying the nucleotide sequence encoding the initiation codon or 5'-UTR of a gene transcript encoding the polypeptide may be achieved, for example, by substituting the nucleotide sequence with a nucleotide sequence encoding another initiation codon having a higher expression rate of the polypeptide compared to the endogenous initiation codon, but is not limited thereto.

The 4) and 5) method of modifying the amino acid sequence or the polynucleotide sequence may be achieved by inducing a modification on the sequence through deletion, insertion, non-conservative or conservative substitution of the amino acid sequence of the polypeptide or the polynucleotide sequence encoding the polypeptide, or a combination thereof to further enhance the activity of the polypeptide, or by replacing the sequence with an amino acid sequence or polynucleotide sequence modified to have a stronger activity, or an amino acid sequence or polynucleotide sequence modified to enhance the activity. The replacement may specifically be performed by inserting the polynucleotide into the chromosome by homologous recombination, but is not limited thereto. The vector used herein may further include a selection marker to confirm the insertion into the chromosome. The selection marker is the same as described above.

The 6) method of introducing a foreign polynucleotide having the activity of the polypeptide may be achieved by introducing into a host cell a foreign polynucleotide encoding a polypeptide that exhibits the same or similar activity to the polypeptide. The foreign polynucleotide may be used without limitation regardless of its origin or sequence as long as it exhibits the same or similar activity to the polypeptide. The introduction may be performed by one of ordinary skill in the art by selecting a transformation method known in the art, and the expression of the introduced polynucleotide in the host cell enables to produce the polypeptide, thereby increasing its activity.

The 7) method of codon-optimization of a polynucleotide encoding the polypeptide may be achieved by codon-optimization of an endogenous polynucleotide to increase the transcription or translation within a host cell, or by optimizing the codons thereof such that the optimized transcription and translation of the foreign polynucleotide can be achieved within the host cell.

The 8) method of analyzing the tertiary structure of the polypeptide and thereby selecting and modifying the exposed site, or chemically modifying the same may be achieved, for example, by comparing the sequence information of the polypeptide to be analyzed with a database, in which the sequence information of known proteins is stored, to determine template protein candidates according to the degree of sequence similarity, and thus confirming the structure based on the information, thereby selecting and transforming or modifying an exposed site to be modified or chemically modified.

Such enhancement of the polypeptide activity may mean that the activity or concentration (expression level) of the polypeptide is increased relative to the activity or concentration of the polypeptide expressed in a wild-type or a microbial strain before modification, or that the amount of product produced from the polypeptide is increased, but is not limited thereto.

The modification of a part or all of the polynucleotide in the microorganism of the present application may be achieved by (a) homologous recombination using a vector for chromosomal insertion in the microorganism or genome editing using engineered nuclease (e.g., CRISPR-Cas9) and/or (b) may be induced by light, such as ultraviolet rays and radiation, etc., and/or chemical treatments, but is not limited thereto. The method of modifying a part or all of the gene may include a method using DNA recombination technology. For example, a part or all of the gene may be deleted by injecting a nucleotide sequence or a vector containing a nucleotide sequence homologous to the target gene into a microorganism to induce homologous recombination. The injected nucleotide sequence or the vector may include a dominant selection marker, but is not limited thereto.

As used herein, the term "weakening" of a polypeptide activity is a comprehensive concept including both reduced or no activity compared to its endogenous activity. The weakening may be used interchangeably with terms such as inactivation, deficiency, down-regulation, decrease, reduce, attenuation, etc.

The weakening may also include a case where the polypeptide activity itself is decreased or removed compared to the activity of the polypeptide originally possessed by a microorganism due to a mutation of the polynucleotide encoding the polypeptide; a case where the overall level of intracellular polypeptide activity and/or concentration (expression level) is decreased compared to a natural strain due to the inhibition of expression of the gene of the polynucleotide encoding the polypeptide, or the inhibition of translation into the polypeptide, etc.; a case where the polynucleotide is not expressed at all; and/or a case where no polypeptide activity is observed even when the polynucleotide is expressed. As used herein, the term "endogenous activity" refers to the activity of a particular polypeptide originally possessed by a parent strain before transformation, a wild-type or a non-modified microorganism, when a trait is altered due to genetic modification caused by a natural or artificial factor, and may be used interchangeably with "activity before modification". The expression 'the polypeptide activity is "inactivated, deficient, decreased, down-regulated, reduced or attenuated" compared to its endogenous activity' means that the polypeptide activity is decreased compared to the activity of a particular polypeptide originally possessed by a parent strain before transformation or a non-modified microorganism.

The weakening of the activity of the polypeptide can be performed by any method known in the art, but the method is not limited thereto, and can be achieved by applying various methods well known in the art (e.g., Nakashima N et al., Bacterial cellular engineering by genome editing and gene silencing. Int J Mol Sci. 2014; 15(2):2773-2793, Sambrook et al. Molecular Cloning 2012, etc.).

Specifically, the weakening of the polypeptide of the present application may be achieved by:

1) deleting a part or all of the gene encoding the polypeptide;
2) modifying the expression regulatory region (expression regulatory sequence) such that the expression of the gene encoding the polypeptide is decreased;
3) modifying the amino acid sequence constituting the polypeptide such that the polypeptide activity is removed or weakened (e.g., deletion/substitution/addition of one or more amino acids on the amino acid sequence).

4) modifying the gene sequence encoding the polypeptide such that the polypeptide activity is removed or weakened (e.g., deletion/substitution/addition of one or more of nucleotides on the nucleotide sequence of the polypeptide gene to encode a polypeptide that has been modified to remove or weaken the activity of the polypeptide;

5) modifying a nucleotide sequence encoding the initiation codon or 5'-UTR of the gene transcript encoding the polypeptide;

6) introducing an antisense oligonucleotide (e.g., antisense RNA), which binds complementary to the transcript of the gene encoding the polypeptide;

7) adding a sequence complementary to the Shine-Dalgarno (SD) sequence on the front end of the SD sequence of the gene encoding the polypeptide to form a secondary structure, thereby inhibiting the ribosomal attachment;

8) a reverse transcription engineering (RTE), which adds a promoter, which is to be reversely transcribed, on the 3' terminus of the open reading frame (ORF) of the gene sequence encoding the polypeptide; or 9) a combination of two or more selected from the methods 1) to 8) above, but is not limited thereto.

For example,

The 1) method of deleting a part or all of the gene encoding the polypeptide may be achieved by deleting all of the polynucleotide encoding the endogenous target polypeptide within the chromosome, or by replacing the polynucleotide with a polynucleotide or a marker gene having a partially deleted nucleic acid sequence.

In addition, the 2) method of modifying the expression regulatory region (expression regulatory sequence) may be achieved by inducing a modification on the expression regulatory region (expression regulatory sequence) through deletion, insertion, non-conservative substitution or conservative substitution, or a combination thereof; or by replacing the sequence with a sequence having a weaker activity. The expression regulatory region may include a promoter, an operator sequence, a sequence encoding a ribosome-binding site, and a sequence for regulating transcription and translation, but is not limited thereto.

In addition, the 5) method of modifying a nucleotide sequence encoding the initiation codon or 5'-UTR of the gene transcript encoding the polypeptide may be achieved, for example, by substituting the nucleotide sequence with a nucleotide sequence encoding another initiation codon having a lower polypeptide expression rate than the endogenous initiation codon, but is not limited thereto.

In addition, the 3) and 4) method of modifying the amino acid sequence or the polynucleotide sequence may be achieved by inducing a modification on the sequence through deletion, insertion, non-conservative or conservative substitution of the amino acid sequence of the polypeptide or the polynucleotide sequence encoding the polypeptide, or a combination thereof to further weaken the activity of the polypeptide, or by replacing the sequence with an amino acid sequence or a polynucleotide sequence modified to have a weaker activity, or an amino acid sequence or a polynucleotide sequence modified to have no activity. For example, the expression of a gene may be inhibited or weakened by introducing a mutation into the polynucleotide sequence to form a stop codon, but is not limited thereto.

The 6) method of introducing an antisense oligonucleotide (e.g., antisense RNA), which binds complementary to the transcript of the gene encoding the polypeptide can be found in the literature [Weintraub, H. et al., Antisense-RNA as a molecular tool for genetic analysis, Reviews—Trends in Genetics, Vol. 1(1) 1986].

The 7) method of adding a sequence complementary to the Shine-Dalgarno (SD) sequence on the front end of the SD sequence of the gene encoding the polypeptide to form a secondary structure, thereby inhibiting the ribosome attachment may be achieved by inhibiting mRNA translation or reducing the speed thereof.

The 8) reverse transcription engineering (RTE), which adds a promoter, which is to be reversely transcribed, on the 3' terminus of the open reading frame (ORF) of the gene sequence encoding the polypeptide may be achieved by forming an antisense nucleotide complementary to the gene transcript encoding the polypeptide to weaken the activity.

In the microorganism of the present application, variants, polynucleotides, vectors and branched-chain amino acids are the same as described in other aspects.

Even another aspect of the present application provides a method for producing branched-chain amino acids, including culturing the microorganism of the genus *Corynebacterium* in a medium.

As used herein, the term "cultivation" means that the microorganism of the genus *Corynebacterium* of the present application is grown under appropriately controlled environmental conditions. The cultivation process of the present application may be performed in a suitable culture medium and culture conditions known in the art. Such a cultivation process may be easily adjusted for use by those skilled in the art according to the strain to be selected. Specifically, the cultivation may be a batch culture, a continuous culture, and/or a fed-batch culture, but is not limited thereto.

As used herein, the term "medium" refers to a mixture of materials which contains nutrient materials required for the cultivation of the microorganism of the genus *Corynebacterium* of the present application as a main ingredient, and it supplies nutrient materials and growth factors, along with water that is essential for survival and growth. Specifically, the medium and other culture conditions used for culturing the microorganism of the genus *Corynebacterium* of the present application may be any medium used for conventional cultivation of microorganisms without any particular limitation. However, the microorganism of the genus *Corynebacterium* of the present application may be cultured under aerobic conditions in a conventional medium containing an appropriate carbon source, nitrogen source, phosphorus source, inorganic compound, amino acid, and/or vitamin, while adjusting temperature, pH, etc.

Specifically, the culture medium for the microorganism of the genus *Corynebacterium* can be found in the literature ["Manual of Methods for General Bacteriology" by the American Society for Bacteriology (Washington D.C., USA, 1981)].

In the present application, the carbon source may include carbohydrates, such as glucose, saccharose, lactose, fructose, sucrose, maltose, etc.; sugar alcohols, such as mannitol, sorbitol, etc.; organic acids, such as pyruvic acid, lactic acid, citric acid, etc.; amino acids, such as glutamic acid, methionine, lysine, etc. Additionally, the carbon source may include natural organic nutrients such as starch hydrolysate, molasses, blackstrap molasses, rice bran, cassava, sugar cane molasses, corn steep liquor, etc. Specifically, carbohydrates such as glucose and sterilized pretreated molasses (i.e., molasses converted to reducing sugar) may be used, and in addition, various other carbon sources in an appropriate amount may be used without limitation. These carbon sources may be used alone or in a combination of two or more kinds, but are not limited thereto.

The nitrogen source may include inorganic nitrogen sources, such as ammonia, ammonium sulfate, ammonium chloride, ammonium acetate, ammonium phosphate, ammonium carbonate, ammonium nitrate, etc.; amino acids, such as glutamic acid, methionine, glutamine, etc.; and organic nitrogen sources, such as peptone, NZ-amine, meat extract, yeast extract, malt extract, corn steep liquor, casein hydrolysate, fish or decomposition product thereof, defatted soybean cake or decomposition product thereof, etc. These nitrogen sources may be used alone or in a combination of two or more kinds, but are not limited thereto.

The phosphorus source may include monopotassium phosphate, dipotassium phosphate, or corresponding sodium-containing salts, etc. Examples of the inorganic compound may include sodium chloride, calcium chloride, iron chloride, magnesium sulfate, iron sulfate, manganese sulfate, calcium carbonate, etc. Additionally, amino acids, vitamins, and/or appropriate precursors may be included. These constituting ingredients or precursors may be added to a medium in a batch or continuous manner, but these phosphorus sources are not limited thereto.

The pH of a medium may be adjusted during the cultivation of the microorganism of the genus *Corynebacterium* by adding a compound such as ammonium hydroxide, potassium hydroxide, ammonia, phosphoric acid, sulfuric acid, etc. to the medium in an appropriate manner. Additionally, during the cultivation, an antifoaming agent such as fatty acid polyglycol ester may be added to prevent foam generation. In addition, oxygen or oxygen-containing gas may be injected into the medium in order to maintain an aerobic state of the medium; or nitrogen, hydrogen, or carbon dioxide gas may be injected without the injection of gas in order to maintain an anaerobic or microaerobic state of the medium, but the gas is not limited thereto.

The medium temperature in the cultivation of the present application may be in a range from 20° C. to 45° C., and specifically, from 25° C. to 40° C., and the cultivation may be carried out for about 10 to 160 hours, but is not limited thereto.

The branched-chain amino acids produced by the cultivation of the present application may be released into the medium or remain in the cells.

The method for preparing branched-chain amino acids of the present application may further include a step of preparing the microorganism of the genus *Corynebacterium* of the present application, a step of preparing a medium for culturing the strain, or a combination thereof (regardless of the order, in any order), for example, prior to the culturing step.

The method for preparing branched-chain amino acids of the present application may further include a step of recovering branched-chain amino acids from the culture medium (medium on which the culture was grown) or the microorganism of the genus *Corynebacterium* of the present application. The recovering step may be further included after the culturing step.

In the recovering step, desired branched-chain amino acids may be collected using the method of culturing a microorganism of the present application, for example, using a suitable method known in the art according to a batch culture, continuous culture, or fed-batch culture method. For example, methods such as centrifugation, filtration, treatment with a protein crystallizing precipitant (salting-out method), extraction, ultrasonic disruption, ultrafiltration, dialysis, various kinds of chromatographies such as molecular sieve chromatography (gel filtration), adsorption chromatography, ion exchange chromatography, affinity chromatography, etc., HPLC or a combination thereof may be used, and the desired branched-chain amino acids can be recovered from the medium or the microorganisms using suitable methods known in the art.

Further, the method for preparing branched-chain amino acids of the present application may further include a purification process, which may be performed using an appropriate method known in the art. In one example, when the method for preparing branched-chain amino acids of the present application includes both a recovering step and a purification step, the recovering step and the purification step may be performed intermittently (or continuously) regardless of the order or simultaneously, or may be integrated into one step, but the method is not limited thereto.

In the method of the present application, variants, polynucleotides, vectors and microorganism are the same as described in other aspects.

Still further another aspect of the present application provides a composition for producing branched-chain amino acids, including the variant of the present application, a polynucleotide encoding the variant, a vector containing the polynucleotide or a microorganism of the genus *Corynebacterium* including the polynucleotide of the present application; a medium containing the same; or a combination of two or more thereof.

The composition of the present application may further include any suitable excipient commonly used in the composition for producing branched-chain amino acids, and such excipient may be, for example, a preservative, a wetting agent, a dispersing agent, a suspending agent, a buffering agent, a stabilizing agent, or an isotonic agent, but is not limited thereto.

In the composition of the present application, variants, polynucleotides, vectors, strains, media and branched-chain amino acids are the same as described in the other aspects.

Still further another aspect of the present application provides use of the branched-chain amino acid production of the aroG aldolase variant of the present application.

Still further another aspect of the present application provides use of the branched-chain amino acid production of the microorganism including one or more of the aroG aldolase variant of the present application; a polynucleotide encoding the aroG aldolase variant; and a vector containing the polynucleotide.

In the use of the present application, variants, polynucleotides, vectors, microorganisms, etc. are the same as described in the other aspects.

MODE FOR CARRYING OUT THE INVENTION

The present application will be described in detail by way of Examples. However, it will be apparent to those skilled in the art that these Examples are given for illustrative purposes only, and are not intended to limit the scope of the invention thereto.

Example 1: Discovery of aroG Aldolase Mutation

Example 1-1. Preparation of Vector Containing aroG Aldolase

In order to prepare an aroG aldolase mutant library having the activity of phospho-2-dehydro-3-deoxyheptonate aldolase, a recombinant vector containing aroG aldolase was first prepared. In order to amplify the aroG gene (SEQ ID NO: 2) encoding the aroG aldolase (SEQ ID NO: 1, KEGG ID: NCgI2098) derived from a wild-type *Corynebacterium glutamicum*, PCR was performed based on the chromosome of the wild-type *Corynebacterium glutamicum* ATCC13032 as a template using the primers of SEQ ID NOS: 11 and 12, under the following conditions: 25 cycles of denaturation at 94° C. for 1 minute, annealing at 58° C. for 30 seconds, and polymerization at 72° C. for 1 minute using Pfu DNA polymerase. The specific sequences of the primers used are shown in Table 1. The amplified product was cloned into an *E. coli* vector pCR2.1 using a TOPO Cloning Kit (Invitrogen) to obtain "pCR-aroG".

TABLE 1

| SEQ ID NO: | Sequence (5'→3') |
|---|---|
| SEQ ID NO: 11 | TGATGCGCGTCATAATTTAG |
| SEQ ID NO: 12 | CTCATCTCTGACTGGACGTG |

Example 1-2. Preparation of aroG Aldolase Mutant Library

Based on the vector prepared in Example 1-1, an aroG aldolase mutation library was prepared using an error-prone PCR kit (clontech Diversify® PCR Random Mutagenesis Kit). PCR reaction was performed using SEQ ID NO: 11 and SEQ ID NO: 12 as primers under conditions in which 0 to 3 mutations per 1000 bp could occur. Specifically, after pre-heating at 94° C. for 30 seconds, the PCR was performed by repeating 25 cycles of denaturation at 94° C. for 30 seconds and annealing at 68° C. for 1 minute and 30 seconds. Using the thus-obtained PCR product obtained as a megaprimer (50 to 125 ng), the PCR was performed by repeating 25 cycles of denaturation at 95° C. for 50 seconds, annealing at 60° C. for 50 seconds, and polymerization at 68° C. for 12 minutes, and the resulting products were treated with DpnI, transformed into *E. coli* DH5a by a heat shock method, and plated onto a LB solid medium containing kanamycin (25 mg/L). 20 kinds of the thus-transformed colonies were selected to obtain plasmids, and the nucleotide sequences were analyzed. As a result, it was confirmed that mutations were introduced at different positions with a frequency of 2 mutations/kb. About 20,000 transformed *E. coli* colonies were collected and plasmids were extracted, and these were named "pTOPO-aroG-library".

Example 2: Evaluation of Prepared Library and Selection of Variants

Example 2-1. Selection of Mutant Strains Having Increased L-Leucine Producing Ability The pTOPO-aroG-library prepared in Example 1-2 was transformed into the wild-type *Corynebacterium glutamicum* ATCC13032 by electroporation, and then plated onto a nutrient medium (Table 2) containing 25 mg/L kanamycin to select 10,000 colonies of strains into which the mutant gene was inserted. Each selected colony was named from ATCC13032/pTOPO_aroG(mt)1 to ATCC13032/pTOPO_aroG(mt) 10,000.

Fermentation titer was evaluated in the following manner for each colony in order to identify colonies in which L-leucine production was increased and L-tyrosine and L-phenylalanine among the aromatic amino acids were decreased among the 10,000 obtained colonies.

TABLE 2

| Type of Medium | Ingredient |
|---|---|
| Production Medium | Glucose 100 g, $(NH_4)_2SO_4$ 40 g, Soy Protein 2.5 g, Corn Steep Solids 5 g, Urea 3 g, $KH_2PO_4$ 1 g, $MgSO_4$•$7H_2O$ 0.5 g, Biotin 100 μg, Thiamine Hydrochloride 1,000 μg, Calcium Pantothenate 2000 μg, Nicotinamide 3,000 μg, $CaCO_3$ 30 g; (based on 1 L of distilled water), pH 7.0 |
| Nutrient Medium | Glucose 10 g, Meat Extract 5 g, Polypeptone 10 g, Sodium Chloride 2.5 g, Yeast Extract 5 g, Agar 20 g, Urea 2 g (Based on 1 L of distilled water) |

A platinum loop of each colony was inoculated into a 250 mL corner-baffled flask containing 25 ug/ml of kanamycin in 25 mL of an autoclaved production medium (Table 2), and then cultured by shaking at 30° C. for 60 hours at 200 rpm. After completion of the culture, the production of L-leucine, and L-tyrosine and L-phenylalanine among aromatic amino acids were measured by high performance liquid chromatography (HPLC, SHIMAZDU LC20A).

Among the thus-obtained 10,000 colonies, the four strains with the most improved L-leucine producing ability compared to the wild-type *Corynebacterium glutamicum* strain (ATCC13032) were selected, which were namely ATCC13032/pTOPO_aroG(mt)2256, ATCC13032/pTOPO_aroG(mt)6531, ATCC13032/pTOPO_aroG(mt) 8316, and ATCC13032/pTOPO_aroG(mt)9426. The concentrations of L-leucine (Leu), L-tyrosine (Tyr), and L-phenylalanine (Phe) produced in the selected strains are shown in Table 3 below.

TABLE 3

| Name of Strains | Leu (g/L) | Tyr (g/L) | Phe (g/L) |
|---|---|---|---|
| ATCC13032 | 0.87 | 1.28 | 1.87 |
| ATCC13032/pTOPO_aroG (mt)2256 | 1.25 | 0.43 | 0.57 |
| ATCC13032/pTOPO_aroG (mt)6531 | 1.23 | 0.15 | 0.19 |
| ATCC13032/pTOPO_aroG (mt)8316 | 1.31 | 0.54 | 0.63 |
| ATCC13032/pTOPO_aroG (mt)9426 | 1.27 | 0.31 | 0.34 |

As shown in Table 3 above, it was confirmed that the *Corynebacterium glutamicum* ATCC13032/pTOPO_aroG (mt)2256 having a mutation in the aroG gene showed an increased L-leucine producing ability by about 1.4 times compared to the *Corynebacterium glutamicum* ATCC13032, the parent strain. In addition, it was confirmed that ATCC13032/pTOPO_aroG(mt)6531, ATCC13032/pTOPO_aroG(mt)8316, ATCC13032/pTOPO_aroG(mt) 9426 showed an improved L-leucine producing ability by about 1.4 times compared to the parent strain. Further, it was confirmed that all four strains of ATCC13032/pTOPO_aroG (mt)2256, ATCC13032/pTOPO_aroG(mt)6531, ATCC13032/pTOPO_aroG(mt)8316, ATCC13032/pTOPO_aroG(mt)9426 showed a decrease in L-tyrosine production by 2.4 to 8.5 times and L-phenylalanine production by 3 to 10 times.

Example 2-2. Confirmation of Mutations in Mutant Strains with Increased L-Leucine Production and Decreased Aromatic Amino Acid Production In order to confirm the aroG gene mutation of the four selected mutant strains, PCR was performed using the primers of SEQ ID NO: 11 and SEQ ID NO: 12 listed in Table 1 based on the DNA of each mutant strain under conditions of denaturation at 94° C. for 5 minutes, followed by 30 cycles of denaturation at 94° C. for 30 seconds, annealing at 55° C. for 30 seconds, and polymerization at 72° C. for 1 minute and 30 seconds, and then polymerization at 72° C. for 5 minutes, and then DNA sequencing was carried out.

As a result of sequencing, it was confirmed that in the ATCC13032/pTOPO_aroG (mt)2256 strain, CGC, which are the 649th, 650th, and 651st nucleotides of the aroG gene, were substituted with GCG. This indicates that a variant (hereinafter, R217A) in which arginine, which is the 217th amino acid of aroG aldolase, was substituted with alanine could be encoded. The amino acid sequence of the aroG aldolase mutant (R217A) and the nucleotide sequence of the aroG aldolase mutant encoding the same are represented by SEQ ID NOS: 3 and 4.

In addition, in the ATCC13032/pTOPO_aroG(mt)6531 strain, it was confirmed that AA, which are the 928th and 929th nucleotides of the aroG gene, were substituted with GC. This indicates that the variant (hereinafter, K310A) in which lysine, which is the 310th amino acid of aroG aldolase, was substituted with alanine could be encoded. The amino acid sequence of the aroG aldolase mutant (K310A) and the nucleotide sequence of the aroG aldolase mutant encoding the same are represented by SEQ ID NOS: 5 and 6.

In the ATCC13032/pTOPO_aroG(mt)8316 strain, it was confirmed that CGC, which are the 1207th to 1209th nucleotides of the aroG gene, were substituted with GCG. This indicates that the variant (hereinafter, R403A) in which arginine, which is the 403rd amino acid of aroG aldolase, was substituted with alanine could be encoded. The amino acid sequence of the aroG aldolase mutant (R403A) and the nucleotide sequence of the aroG aldolase mutant encoding the same are represented by SEQ ID NOS: 7 and 8.

In the ATCC13032/pTOPO_aroG(mt)9426 strain, it was confirmed that AA, which are the 1385th and 1386th nucleotides of the DAHP gene, were substituted with CG. This indicates that the mutant (hereinafter, E462A) in which glutamate, which is the 462nd amino acid of aroG aldolase, was substituted with alanine could be encoded. The amino acid sequence of the aroG aldolase mutant (E462A) and the nucleotide sequence of the aroG aldolase mutant encoding the same are represented by SEQ ID NOS: 9 and 10.

Therefore, in the following Examples, experiments were conducted to determine whether the mutations (R217A, K310A, R403A, E462A) affect the production of L-leucine and aromatic amino acids in microorganisms of the genus *Corynebacterium.*

Example 3: Confirmation of L-Leucine, L-Tyrosine, and L-Phenylalanine Producing Ability of Selected Mutant Strains

Example 3-1. Preparation of Insertion Vectors Containing aroG Aldolase Mutation In order to introduce the mutations selected in Example 2 into the strains, insertion vectors were prepared. Site directed mutagenesis was used to prepare vectors for introducing aroG (R217A, K310A, R403A, E462A) mutations. PCR was performed using the primer pairs of SEQ ID NOS: 13 and 14 and SEQ ID NOS: 15 and 16 to produce the R217A mutation, and using the primer pairs of SEQ ID NOS: 13 and 17 and SEQ ID NOS: 15 to 18 to produce the K310A mutation based on the chromosome of the wild-type *Corynebacterium glutamicum* ATCC13032 as a template. Additionally, PCR was performed using the primer pairs of SEQ ID NOS: 13 and 19 and SEQ ID NOS: 15 and 20 to produce the R403A mutation, and using the primer pairs of SEQ ID NOS: 13 and 21 and SEQ ID NOS: 15 to 22 to produce the E462A mutation. Specifically, the PCR was performed under conditions of denaturation at 94° C. for 5 minutes, followed by 30 cycles of denaturation at 94° C. for 30 seconds, annealing at 55° C. for 30 seconds, and polymerization at 72° C. for 1 minute and 30 seconds, and then polymerization at 72° C. for 5 minutes. The specific sequences of the primers used are shown in Table 4.

TABLE 4

| SEQ ID NO: | Sequence (5'→3') |
|---|---|
| SEQ ID NO: 13 | GTGAATTCGAGCTCGGTACCCAGTTGAATGCTACCAACTTG |
| SEQ ID NO: 14 | CACGAGCAAGAGCCTCGTAcgcTGCACCAGCTGGG |
| SEQ ID NO: 15 | GGTCGACTCTAGAGGATCCCCGCTGTTATTACTGTGCCTG |
| SEQ ID NO: 16 | GAACTCCCCAGCTGGTGCAgcgTACGAGGCTCTTGCTCG |
| SEQ ID NO: 17 | GGGTGATACCAGGACCAATcgcGATGCCGATTGGGTTAG |
| SEQ ID NO: 18 | CTCTAACCCAATCGGCATCgcgATTGGTCCTGGTATCAC |
| SEQ ID NO: 19 | CTGGGTGGGTGCCCAATGCcgcGTGGACCTCGAAGAAG |
| SEQ ID NO: 20 | GGGCTTCTTCGAGGTCCACgcgGCATTGGGCACCCAC |
| SEQ ID NO: 21 | AAGCTTAGTTACGCAGCATcgcTGCAACGAGGAAAGCC |
| SEQ ID NO: 22 | GTTGGCTTTCCTCGTTGCAgcgATGCTGCGTAACTAAGC |

The resulting PCR products were cloned by fusion of the homologous sequence of the terminal 15 bases between the DNA fragments using the linear pDCM2 vector (Korean Patent Publication KR 10-2020-0136813 A) digested with SmaI restriction enzyme and the In-Fusion enzyme to prepare vectors for substituting amino acids, namely, 'pDCM2-aroG(R217A)', 'pDCM2-aroG (K310A)', 'pDCM2-aroG (R403A)', and 'pDCM2-aroG(E462A)'. In addition, the vectors for substituting amino acid at positions 217, 310, 403, and 462 of aroG, 'pDCM2-aroG (R217A, K310A, E462A)' and 'pDCM2-aroG (R217A, K310A, R403A, E462A)', were prepared by the combination of the variants. The amino acid sequence of the aroG aldolase variants (R217A, K310A, E462A) and the nucleotide sequence of the aroG aldolase variants encoding the same are represented by SEQ ID NOS: 23 and 24. Further, the amino acid sequences of the aroG aldolase variants (R217A, K310A, R403A, E462A) and the nucleotide sequences of the aroG aldolase variants encoding the same are represented by SEQ ID NOS: 25 and 26.

Example 3-2. Introduction of Variants into ATCC13032 Strain and Evaluation Thereof The pDCM2-aroG (R217A), pDCM2-aroG (K310A), pDCM2-aroG (R403A), pDCM2-aroG (E462A), pDCM2-aroG (R217A, K310A, E462A), and pDCM2-aroG (R217A, K310A, R403A, E462A) vectors prepared in Example 3-1 were transformed into ATCC13032 by electroporation, and the strains into which the vectors were inserted into the chromosome by recombination of the homologous sequence were selected in a medium containing 25 mg/L kanamycin. The selected primary strains were again subjected to secondary crossover, and strains into which the mutation of the target gene was introduced were selected. The introduction of the aroG gene mutation into the finally transformed strains was confirmed by performing PCR using the primers of SEQ ID NO: 11 and SEQ ID NO: 12 listed in Table 1 and then analyzing the nucleotide sequences. A total of 5 strains were produced, which were named ATCC13032_aroG_R217A, ATCC13032_aroG_K310A, ATCC13032_aroG_R403A, ATCC13032_aroG_E462A, ATCC13032_aroG_(R217A, K310A, E462A), and ATCC13032_aroG_(R217A, K310A, R403A, E462A).

Flask fermentation titer was evaluated in order to evaluate the producing ability of L-leucine and aromatic amino acids in the total of 6 strains prepared above. One platinum loop of each of the parent strain *Corynebacterium glutamicum* ATCC13032, and ATCC13032_aroG_R217A, ATCC13032_aroG_K310A, ATCC13032_aroG_R403A, ATCC13032_aroG_E462A, ATCC13032_aroG_(R217A, K310A, E462A), and ATCC13032_aroG_(R217A, K310A, R403A, E462A) prepared above was inoculated into a 250 mL corner-baffled flask containing 25 mL of production medium, and then cultured with shaking at 200 rpm at 30° C. for 60 hours to produce L-leucine. After completion of the culture, the production of L-leucine, L-tyrosine and L-phenylalanine was measured by HPLC. The leucine concentration in the culture medium for each strain tested is shown in Table 5 below.

TABLE 5

| Name of Strain | Leu (g/L) | Tyr (g/L) | Phe (g/L) |
|---|---|---|---|
| ATCC13032 | 0.87 | 1.28 | 1.87 |
| ATCC13032_aroG_R217A | 1.17 | 0.41 | 0.54 |
| ATCC13032_aroG_K310A | 1.19 | 0.15 | 0.13 |
| ATCC13032_aroG_R403A | 1.25 | 0.48 | 0.65 |
| ATCC13032_aroG_E462A | 1.27 | 0.28 | 0.32 |
| ATCC13032_aroG_(R217A, K310A, E462A) | 1.35 | 0.32 | 0.25 |
| ATCC13032_aroG_(R217A, K310A, R403A, E462A) | 1.30 | 0.28 | 0.30 |

As shown in Table 5 above, it was confirmed that ATCC13032_aroG_R217A, ATCC13032_aroG_K310A, ATCC13032_aroG_R403A, ATCC13032_aroG_E462A, ATCC13032_aroG_(R217A, K310A, E462A), and ATCC13032_aroG_(R217A, K310A, R403A, E462A) showed an improved yield of L-leucine by about 1.35 times to 1.55 times compared to the parent strain, *Corynebacterium glutamicum* ATCC13032. In addition, it was confirmed that the yield of L-tyrosine was reduced by 2.5 to 8.5 times, and the yield of L-phenylalanine was reduced by about 3.5 to 14 times.

Example 4: Confirmation of Leucine, Tyrosine, and Phenylalanine-Producing Ability of aroG-Selected Mutations in Leucine-Producing Strain Even if the wild-type strain of the genus *Corynebacterium* is able to produce leucine, only a very trace amount is produced. Accordingly, an experiment was conducted to prepare a leucine-producing strain derived from ATCC13032 and to introduce the selected mutations to confirm the leucine, tyrosine, and phenylalanine-producing abiltiy. The specific experiment was conducted as follows.

Example 4-1. Preparation of L-Leucine-Producing Strain CJL-8109

As a strain for producing high-concentration of L-leucine, a strain derived from ATCC13032 containing: (1) a mutation (R558H) in which G, the 1673rd nucleotide of the IeuA gene, is substituted with A, and arginine, the 558th amino acid of the LeuA protein, is substituted with histidine; (2) a mutation (G561D) in which GC, the 1682 and 1683 nucleotides of the IeuA gene, are substituted with AT, and glycine, the 561st amino acid, is substituted with aspartic acid; and (3) a mutation (P247C) in which CC, the 739th and 740th nucleotides of the leuA gene, are substituted with TG, and proline, the 247th amino acid, is substituted with cysteine, was prepared.

Specifically, the vector pDCM2-leuA(P247C, R558H, G561D) containing the IeuA gene mutation was transformed into the *Corynebacterium glutamicum* ATCC13032 by electroporation, and a strain into which the vector was inserted into the chromosome by recombination of the homologous sequence was selected in a medium containing 25 mg/L kanamycin. The selected primary strain was again subjected to secondary crossover, and a strain into which the IeuA gene mutation was introduced was selected. The introduction of the mutation into the finally the transformed strain was confirmed by performing PCR using the primers of SEQ ID NO: 27 and SEQ ID NO: 28 of Table 6 under conditions of denaturation at 94° C. for 5 minutes, followed by 30 cycles of denaturation at 94° C. for 30 seconds, annealing at 55° C. for 30 seconds, and polymerization at 72° C. for 1 minute and 30 seconds, and then polymerization at 72° C. for 5 minutes, and analyzing the nucleotide sequences. The ATCC13032_leuA_(P247C, R558H, G561D) strain transformed with the vector pDCM2-leuA(P247C, R558H, G561D) was named "CJL-8105".

TABLE 6

| SEQ ID NO: | Sequence (5'→3') |
|---|---|
| 27 | TATGCTTCACCACATGACTTC |
| 28 | AAATCATTTGAGAAAACTCGAGG |

In order to increase the L-leucine producing ability in the thus-prepared CJL-8105 strain, a strain in which the ilvE mutant (V156A), a gene encoding a branched-chain amino acid aminotransferase, was introduced was prepared (Korean Patent No. 10-2143964). Specifically, the pDCM2-ilvE (V156A) vector containing the ilvE gene mutation was transformed into the *Corynebacterium glutamicum* CJL-8105 by electroporation, and a strain into which the vector was inserted into the chromosome by recombination of the homologous sequence was selected in a medium containing 25 mg/L kanamycin. The selected primary strains were again subjected to secondary crossover, and a strain into which the ilvE gene mutation was introduced was selected. The introduction of the mutation into the finally transformed strain was confirmed by performing PCR using the primers of SEQ ID NO: 29 and SEQ ID NO: 30 of Table 7 under conditions of denaturation at 94° C. for 5 minutes, followed by 30 cycles of denaturation at 94° C. for 30 seconds, annealing at 55° C. for 30 seconds, and polymerization at 72° C. for 1 minute and 30 seconds, and then polymerization at 72° C. for 5 minutes, and analyzing the nucleotide sequences, thereby confirming the introduction of V156A mutation. The strain transformed with the pDCM2-ilvE (V156A) vector was named "CJL-8108".

TABLE 7

| SEQ ID NO: | Sequence (5'→3') |
|---|---|
| 29 | GTCACCCGATCGTCTGAAG |
| 30 | GTCTTAAAACCGGTTGAT |

In order to increase L-leucine producing ability in the thus-prepared CJL-8108 strain, a strain introduced with the gltA mutant (M3121; SEQ ID NO: 41) having weakened citrate synthase activity was prepared. Specifically, the pDCM2-gltA(M3121) vector containing the gltA gene mutation was transformed into the *Corynebacterium glutamicum* CJL-8108 by electroporation, and a strain into which the vector was inserted into the chromosome by recombination of the homologous sequence was selected in a medium containing 25 mg/L kanamycin. The selected primary strain was again subjected to secondary crossover, and a strain into which the gltA gene mutation was introduced were selected. The introduction of the mutation into the finally transformed strain was confirmed by performing PCR using the primers of SEQ ID NO: 31 and SEQ ID NO: 32 of Table 8 under conditions of denaturation at 94° C. for 5 minutes, followed by 30 cycles of denaturation at 94° C. for 30 seconds, annealing at 55° C. for 30 seconds, and polymerization at 72° C. for 1 minute and 30 seconds, and then polymerization at 72° C. for 5 minutes, and analyzing the nucleotide sequences, thereby confirming the introduction of M3121 mutation. The strain transformed with the pDCM2-gltA(M3121) vector was named "CJL-8109".

TABLE 8

| SEQ ID NO: | Sequence (5'→3') |
|---|---|
| 31 | CAATGCTGGCTGCGTACGC |
| 32 | CTCCTCGCGAGGAACCAACT |

Example 4-2. Introduction of aroG Aldolase Variant in CJL-8109 Strain and Evaluation Thereof CJL-8109, which is a leucine-producing strain, was transformed with the vectors pDCM2-aroG(R217A), pDCM2-aroG(K310A), pDCM2-aroG(R403A), pDCM2-aroG (E462A), pDCM2-aroG(R217A, K310A, E462A), and pDCM2-aroG(R217A, K310A, R403A, E462A) prepared in Example 3-1, and strains into which the vectors were inserted into the chromosome by recombination of the homologous sequence were selected in a medium containing 25 mg/L kanamycin. The selected primary strains were again subjected to secondary crossover, and strains into which the mutation of the target gene was introduced were selected. The introduction of the aroG gene mutation into the finally the transformed strain was confirmed by performing PCR using the primers of SEQ ID NO: 11 and SEQ ID NO: 12 and analyzing the nucleotide sequences, thereby confirming the introduction of the aroG aldolase mutations into the strains. The prepared CJL-8109_aroG_R217A was named CJL-8110, CJL-8109_aroG_K310A was named CJL-8111, CJL-8109_aroG_R403A was named CJL-8112, CJL-8109_aroG_E462A was named CJL-8113, CJL-8109_aroG2R217A, K310A, E462A) was named CA13-8114, and CJL-8109_aroG2R217A, K310A, R403A, E462A) was named CJL-8115.

The leucine producing ability of the thus-prepared CJL-8110, CJL-8111, CJL-8112, CJL-8113, CA13-8114, CJL-8115 and ATCC13032, CJL-8109 strains was evaluated. The flask culture was carried out in the same manner as in Example 2, and the production of leucine and aromatic amino acids was measured by HPLC after completion of the culture, and the culture results are shown in Table 9 below.

TABLE 9

| Name of Strains | Leu (g/L) | Tyr (g/L) | Phe (g/L) |
|---|---|---|---|
| ATCC13032 | 0.87 | 1.28 | 1.87 |
| CJL-8109 | 2.77 | 1.08 | 1.57 |
| CJL8109__aroG__R217A:CJL-8110 | 3.55 | 0.31 | 0.49 |
| CJL8109__aroG__K310A:CJL-8111 | 3.36 | 0.12 | 0.10 |
| CJL8109__aroG__R403A:CJL-8112 | 3.65 | 0.35 | 0.56 |
| CJL8109__aroG__E462A:CJL-8113 | 3.78 | 0.21 | 0.25 |
| CJL8109__aroG__(R217A, K310A, E462A):CA13-8114 | 3.85 | 0.19 | 0.22 |
| CJL-8109__aroG__(R217A, K310A, R403A, E462A):CJL-8115 | 3.80 | 0.19 | 0.23 |

As shown in Table 9, the L-leucine-producing strains of *Corynebacterium glutamicum* CJL-8110, CJL-8111, CJL-8112, CJL-8113, CA13-8114, and CJL-8115 having additional R217A, K310A, R403A, and E462A mutations in the aroG gene showed an increased leucine production by about 4 to 5 times compared to the parent strain, *Corynebacterium glutamicum* ATCC13032. In addition, the L-leucine-producing strains of *Corynebacterium glutamicum* CJL-8110, CJL-8111, CJL-8112, CJL-8113, CA13-8114, and CJL-8115 showed an improved L-leucine producing ability by about 1.2 to 1.6 times, and reduced L-tyrosine producing ability and L-phenylalanine producing ability by about 10 to 20 times, compared to the parent strain, *Corynebacterium glutamicum* CJL-8109. From the above results, it can be confirmed that the amino acids at positions 217, 310, 403, and 462 in the amino acid sequence of aroG aldolase are important positions for the production of L-leucine, and L-tyrosine and L-phenylalanine, the aromatic amino acids.

The thus-prepared strain CA13-8114 was deposited at the Korean Culture Center of Microorganisms (KCCM), an International Depositary Authority, under the Budapest Treaty on Jan. 18, 2021 with Accession No. KCCM12931P.

Example 5. Confirmation of Leucine, Tyrosine, and Phenylalanine Producing Ability of aroG-selected Mutation in Isoleucine-Producing Strain In order to confirm whether the selected mutations show an effect on isoleucine, which is a representative branched-chain amino acid as leucine, an experiment was conducted to confirm the isoleucine producing ability by introducing the mutations into an isoleucine-producing strain of the genus *Corynebacterium*. The specific experiments were conducted as follows.

Example 5-1. Preparation of L-Isoleucine-Producing Strain CA10-3101

A L-isoleucine-producing strain was developed from the wild-type *Corynebacterium glutamicum* ATCC13032. Specifically, in order to release the feedback inhibition of threonine, a precursor of isoleucine in the biosynthetic pathway, arginine, the 407th amino acid of horn, a gene encoding homoserine dehydrogenase, was substituted with histidine (US 2020-0340022 A1). Specifically, in order to prepare strains introduced with hom(R407H), PCR was performed using the primer pairs of SEQ ID NOS: 33 and 34 or SEQ ID NOS: 35 and 36 based on the chromosome of *Corynebacterium glutamicum* ATCC13032 as a template. The primer sequences used herein are shown in Table 10 below.

TABLE 10

| SEQ ID NO: | Sequence (5'→3') |
|---|---|
| 33 | TCGAGCTCGGTACCCCGCTTTTGCACTCATCGAGC |
| 34 | CACGATCAGATGTGCATCATCAT |
| 35 | ATGATGATGCACATCTGATCGTG |
| 36 | CTCTAGAGGATCCCCGAGCATCTTCCAAAACCTTG |

PfuUltra™ high-reliability DNA polymerase (Stratagene) was used as the polymerase for the PCR reaction, and PCR was performed by repeating 28 cycles of denaturation at 95° C. for 30 seconds, annealing at 55° C. for 30 seconds, and polymerization at 72° C. for 1 minute. As a result, a DNA fragment (1000 bp) in the 5' upstream region and a DNA fragment (1000 bp) in the 3' downstream region were each obtained around the mutation of the horn gene. PCR was carried out based on the two amplified DNA fragments as a template using the primers of SEQ ID NO: 34 and SEQ ID NO: 35 under conditions of denaturation at 95° C. for 5 minutes, followed by 28 cycles of denaturation at 95° C. for 30 seconds, annealing at 55° C. for 30 seconds, and polymerization at 72° C. for 2 minutes, and then polymerization at 72° C. for 5 minutes.

As a result, the DNA fragment (2 kb) including the mutation of horn gene, which encodes a homoserine dehydrogenase variant in which arginine at position 407 was substituted with histidine, was amplified. The amplified product was purified using a PCR purification kit (QIAGEN) and used as an insert DNA fragment for the preparation of a vector. Meanwhile, after treating the purified amplified product with restriction enzyme SmaI, the ratio of the molar concentration (M) of the pDCM2 vector heat-treated at 65° C. for 20 minutes to the insert DNA fragment, the amplified product, was set to be 1:2, and the vector was cloned using an Infusion Cloning Kit (TaKaRa) according to the manufacturer's manual to thereby prepare the pDCM2-R407H vector for introducing the hom(R407H) mutation into the chromosome.

The thus-prepared vector was transformed into the *Corynebacterium glutamicum* ATCC13032 by electroporation and subjected to secondary crossover, to obtain a strain in including the hom(R407H) mutation on the chromosome, and the strain was named *Corynebacterium glutamicum* ATCC13032 hom(R407H).

In order to release the feedback on L-isoleucine and increase the activity in the prepared ATCC13032 hom (R407H), a strain introduced with the ilvA mutant (T381A, F383A), which is a gene encoding L-threonine dehydratase, was prepared. More specifically, in order prepare strains introduced with the ilvA(T381A, F383A) mutations, PCR was performed using the primer pairs of SEQ ID NOS: 37 and 38 or SEQ ID NOS: 39 and 40 based on the chromosome of *Corynebacterium glutamicum* ATCC13032 as a template. The primer sequences used herein are shown in Table 11 below.

TABLE 11

| SEQ ID NO: | Sequence (5'→3') |
|---|---|
| 37 | TCGAGCTCGGTACCCATGAGTGAAACATACGTGTC |
| 38 | GCGCTTGAGGTACTCtgcCAGCGcGATGTCATCATCCGG |
| 39 | CCGGATGATGACATCgCGCTGgcaGAGTACCTCAAGCGC |
| 40 | CTCTAGAGGATCCCCCGTCACCGACACCTCCACA |

PfuUltra™ high-reliability DNA polymerase (Stratagene) was used as the polymerase for the PCR reaction, and PCR was performed by repeating 28 cycles of denaturation at 95° C. for 30 seconds, annealing at 55° C. for 30 seconds, and polymerization at 72° C. for 1 minute. As a result, a DNA fragment (1126 bp) in the 5' upstream region and a DNA fragment (286 bp) in the 3' downstream region were each obtained around the mutation of the ilvA gene. PCR was carried out based on the two amplified DNA fragments as a template using the primers of SEQ ID NO: 37 and SEQ ID NO: 40 under conditions of denaturation at 95° C. for 5 minutes, followed by 28 cycles of denaturation at 95° C. for 30 seconds, annealing at 55° C. for 30 seconds, and polymerization at 72° C. for 2 minutes, and then polymerization at 72° C. for 5 minutes.

As a result, the DNA fragment (1.4 kb) including the mutation of ilvA gene, which encodes a threonine dehydrogenase variant in which threonine at position 381 was substituted with alanine and phenylalanine at position 383 was substituted with alanine, was amplified. The amplified product was purified using a PCR purification kit (QIAGEN) and used as an insert DNA fragment for the preparation of a vector. Meanwhile, after treating the purified amplified product with restriction enzyme SmaI, the ratio of the molar concentration (M) of the pDCM2 vector heat-treated at 65° C. for 20 minutes to the insert DNA fragment, the amplified product, was set to be 1:2, and the vector was cloned using an Infusion Cloning Kit (TaKaRa) according to the manufacturer's manual to thereby prepare the pDCM2-ilvA (T381A, F383A) vector for introducing the ilvA(T381A, F383A) mutation into the chromosome. The thus-prepared vector was transformed into the *Corynebacterium glutamicum* ATCC13032 hom(R407H) by electroporation and subjected to secondary crossover to obtain a strain including the ilvA(T381A, F383A) mutation on the chromosome, and the strain was named *Corynebacterium glutamicum* CA10-3101.

Example 5-2. Introduction of aroG Aldolase Variants into CA10-3101 Strain and Evaluation Thereof CA10-3101, which is an L-isoleucine-producing strain, was transformed with the vectors pDCM2-aroG (R217A), pDCM2-aroG(K310A), pDCM2-aroG(R403A), pDCM2-aroG(E462A), pDCM2-aroG(R217A, K310A, E462A), and pDCM2-aroG(R217A, K310A, R403A, E462A) prepared in Example 3-1, and strains into which the vectors were inserted into the chromosome by recombination of the homologous sequence were selected in a medium containing 25 mg/L kanamycin. The selected primary strains were again subjected to secondary crossover, and strains into which the mutation of the target gene was introduced were selected. The introduction of the aroG gene mutation into the finally transformed strains was confirmed by performing PCR using the primers of SEQ ID NO: 11 and SEQ ID NO: 12 and analyzing the nucleotide sequences, thereby confirming the introduction of the aroG aldolase mutations into the strains.

The thus-prepared strains were named CA10-3101_aroG_R217A, CA10-3101_aroG_K310A, CA10-3101_aroG_R403A, CA10-3101_aroG_E462A, CA10-3101_aroG2R217A, K310A, E462A), and CA10-3101_aroG2R217A, K310A, R403A, E462A).

The L-isoleucine producing ability of the prepared strains CA10-3101_aroG_R217A, CA10-3101_aroG_K310A, CA10-3101_aroG_R403A, CA10-3101_aroG_E462A, CA10-3101_aroG2R217A, K310A, E462A), CA10-3101_aroG2R217A, K310A, R403A, E462A), and ATCC13032, CA10-3101 was evaluated. L-Isoleucine was prepared by inoculating the parent strain and the aroG aldolase mutant strains into a 250 mL corner-baffled flask containing 25 mL of an isoleucine production medium, and then culturing with shaking at 32° C. for 60 hours at 200 rpm.

The composition of the production medium used in this Example is as follows.

<Production Medium>

Glucose 10%, Yeast Extract 0.2%, $(NH_4)_2SO_4$ 1.6%, $KH_2PO_4$ 0.1%, $MgSO_4 \cdot 7H_2O$ 0.1%, $FeSO_4 \cdot 7H_2O$ 10 mg/L, $MnSO_4 \cdot H_2O$ 10 mg/L, Biotin 200 μg/L, pH 7.2

After completion of the culture, the production of L-isoleucine and by-products was measured using high-performance liquid chromatography (HPLC), and the concentrations of L-isoleucine and by-products in the culture medium for each strain tested are shown in Table 12 below.

TABLE 12

| | Concentration of L-Isoleucine (g/L) | Concentration of L-Tyr (g/L) | Concentration of L-Phe (g/L) |
|---|---|---|---|
| ATCC13032 | 0.0 | 1.2 | 1.5 |
| CA10-3101(Parent strain) | 2.2 | 0.3 | 0.6 |
| CA10-3101_aroG_R217A | 2.5 | 0.0 | 0.1 |
| CA10-3101_aroG_K310A | 2.3 | 0.0 | 0.0 |
| CA10-3101_aroG_R403A | 2.5 | 0.0 | 0.1 |
| CA10-3101_aroG_E462A | 2.6 | 0.0 | 0.0 |
| CA10-3101_aroG_(R217A, K310A, E462A) | 2.6 | 0.0 | 0.0 |
| CA10-3101_aroG_(R217A, K310A, R403A, E462A) | 2.7 | 0.0 | 0.0 |

As shown in Table 12, the L-isoleucine-producing strains having additional R217A, K310A, R403A, and E462A mutations in the aroG gene showed an increased L-isoleucine producing ability by about 1.1 to 1.2 compared to the parent strain, *Corynebacterium glutamicum* CA10-3101, and decreased L-tyrosine producing ability and L-phenylalanine producing ability.

From the above results, it can be confirmed that the amino acids at positions 217, 310, 403, and 462 in the amino acid sequence of the aroG aldolase are important positions for the production of L-isoleucine, and L-tyrosine and L-phenylalanine, which are aromatic amino acids.

Example 6: Confirmation of Valine Producing Ability of aroG-Selected Mutant in Valine-Producing Strain In order to confirm whether the selected mutations have an effect on L-valine, which is a representative branched-chain amino acid as leucine, the selected mutations were also introduced into the valine-producing strain KCCM11201P of the genus *Corynebacterium* to confirm the valine producing ability. Specific experiments were conducted as follows.

Example 6-1. Introduction of aroG Aldolase Variants into KCCM11201P Strain and Evaluation Thereof In order to determine whether the mutations were effective in increasing the valine producing ability, *Corynebacterium glutamicum* KCCM11201P (U.S. Pat. No. 8,465,962 B2), an L-valine-producing strain, was used. KCCM11201P, which is the valine-producing strain, was transformed with the vectors pDCM2-aroG (R217A), pDCM2-aroG(K310A), pDCM2-aroG(R403A), pDCM2-aroG(E462A), pDCM2-aroG(R217A, K310A, E462A), and pDCM2-aroG(R217A, K310A, R403A, E462A) prepared in Example 3-1, and strains into which the vectors were inserted into the chromosome by recombination of the homologous sequence were selected in a medium containing 25 mg/L kanamycin. The selected primary strains were again subjected to secondary crossover, and strains into which the mutation of the target gene was introduced were selected. The introduction of the aroG gene mutation into the finally transformed strains was confirmed by performing PCR using the primers of SEQ ID NO: 11 and SEQ ID NO: 12 and analyzing the nucleotide sequences, thereby confirming the introduction of the aroG aldolase mutations into the strains. The thus-prepared strains were named KCCM11201P-aroG(R217A), KCCM11201P-aroG(K310A), KCCM11201P-aroG (R403A), KCCM11201P-aroG(E462A), KCCM11201P-aroG(R217A, K310A, E462A), and KCCM11201P-aroG (R217A, K310A, R403A, E462A).

The valine producing ability of the prepared strains KCCM11201P-aroG(R217A), KCCM11201P-aroG (K310A), KCCM11201P-aroG (R403A), KCCM11201P-aroG (E462A), KCCM11201P-aroG(R217A, K310A, E462A), and KCCM11201P-aroG(R217A, K310A, R403A, E462A) was evaluated. The flask culture was carried out in the same manner as in Example 2, and the valine production was measured by HPLC after completion of the culture, and the culture results are shown in Table 13 below.

TABLE 13

| Name of Strain | Val (g/L) | Tyr (mg/L) | Phe (mg/L) |
|---|---|---|---|
| KCCM11201P | 2.60 | 58.25 | 146.62 |
| KCCM11201P - aroG(R217A) | 2.67 | 16.72 | 45.76 |
| KCCM11201P - aroG (K310A) | 2.81 | 6.47 | 9.34 |
| KCCM11201P - aroG (R403A) | 2.74 | 18.88 | 52.30 |
| KCCM11201P - aroG (E462A) | 2.84 | 11.33 | 23.35 |
| KCCM11201P - aroG(R217A, K310A, E462A) | 2.85 | 10.25 | 21.34 |

TABLE 13-continued

| Name of Strain | Val (g/L) | Tyr (mg/L) | Phe (mg/L) |
|---|---|---|---|
| KCCM11201P - aroG(R217A, K310A, R403A, E462A) | 2.89 | 10.25 | 20.55 |

As shown in Table 13 above, the L-valine-producing strains of *Corynebacterium glutamicum* KCCM11201P-aroG (R217A), KCCM11201P-aroG (K310A), KCCM11201P-aroG (R403A), KCCM11201P-aroG (E462A), KCCM11201P-aroG(R217A, K310A, E462A), and KCCM11201P-aroG (R217A, K310A, R403A, E462A) having additional R217A, K310A, R403A, and E462A mutations in the aroG gene showed an increased valine producing ability by a maximum of 1.11 times and decreased L-tyrosine producing ability and L-phenylalanine producing ability by about 10 to 20 times, compared to the parent strain, *Corynebacterium glutamicum* KCCM11201P.

From the above results, it can be confirmed that the amino acids at positions 217, 310, 403, and 462 in the amino acid sequence of aroG aldolase are important positions for the production of L-valine, and L-tyrosine and L-phenylalanine, which are aromatic amino acids.

Reference Example 1: Confirmation of Leucine Production of gltA(M3121) Mutation

Reference Example 1-1. Preparation of Insertion Vector Containing gltA Mutation Site directed mutagenesis was used to prepare a vector for introducing gltA (M3121; SEQ ID NO: 41) mutation.

PCR was performed using the primer pairs of SEQ ID NOS: 43 and 44 and SEQ ID NOS: 45 and 46 based on the chromosome of the wild-type *Corynebacterium glutamicum*. The PCR was performed under conditions of denaturation at 94° C. for 5 minutes, followed by 30 cycles of denaturation at 94° C. for 30 seconds, annealing at 55° C. for 30 seconds, and polymerization at 72° C. for 1 minute and 30 seconds, and then polymerization at 72° C. for 5 minutes. The resulting gene fragments were cloned by fusion of the homologous sequence of the terminal 15 bases between the DNA fragments using the linear pDCM2 vector digested with SmaI restriction enzyme and the In-Fusion enzyme to prepare the pDCM2-gltA(M3121) vector for substituting methionine, which is the 312th amino acid, with isoleucine.

TABLE 14

| SEQ ID NO: | Primer | Sequence (5'→3') |
|---|---|---|
| 43 | gltA M3121 Up F | GTGAATTCGAGCTCGGTACCC GCGGGAATCCTGCGTTACCGC |
| 44 | gltA M3121 Up R | TGTAAACGCGGTGTCCGAAGC CGATGAGGCGGACGCCGTCTT |
| 45 | gltA M3121 Down F | AAGACGGCGTCCGCCTCATCG GCTTCGGACACCGCGTTTACA |
| 46 | gltA M3121 Down R | GGTCGACTCTAGAGGATCCCC TTAGCGCTCCTCGCGAGGAAC |

Reference Example 1-2. Introduction of Variants into ATCC13032 Strain and Evaluation Thereof The vector pDCM2-gltA(M3121) was transformed into the wild-type ATCC13032, and a strain into which the vector was inserted into the chromosome by recombination of the homologous sequence was selected in a medium containing 25 mg/L kanamycin. The selected primary strain was again subjected to secondary crossover, and a strain into which the mutation of the target gene was introduced was selected. The introduction of the gltA gene mutation into the finally transformed strain was confirmed by performing PCR using the primers of SEQ ID NO: 31 and SEQ ID NO: 32 (Example 4-1, Table 8) and analyzing the nucleotide sequences, thereby confirming that the introduction of the mutation (SEQ ID NO: 42) into the strain. The thus-prepared strain was named ATCC13032_gltA_M3121.

Flask fermentation titer was evaluated in order to evaluate the leucine producing ability of the ATCC13032_gltA_M3121 strain prepared above. One platinum loop of each of the parent strain *Corynebacterium glutamicum* ATCC13032 and ATCC13032_gltA_M3121 prepared above was inoculated into a 250 mL corner-baffled flask containing 25 mL of production medium, and then cultured with shaking at 200 rpm at 30° C. for 60 hours to produce leucine. After completion of the culture, the leucine production was measured by HPLC. The leucine concentration in the culture medium for each strain tested is shown in Table 15 below.

Production Medium: Glucose 100 g, $(NH_4)_2SO_4$ 40 g, Soy Protein 2.5 g, Corn Steep Solids 5 g, Urea 3 g, $KH_2PO_4$ 1 g, $MgSO_4 \cdot 7H_2O$ 0.5 g, Biotin 100 μg, Thiamine Hydrochloride 1,000 μg, Calcium Pantothenate 2000 μg, Nicotinamide 3,000 μg, $CaCO_3$ 30 g (based on 1 L of distilled water), pH 7.0

TABLE 15

| Name of Strain | Leucine (g/L) |
|---|---|
| ATCC13032 | 0.87 |
| ATCC13032_gltA_M312I | 1.25 |

Based on the results, it was confirmed that the M3121 substitution of gltA is an effective mutation for increasing leucine production.

Reference Example 2: Confirmation of Isoleucine Production of ilvA(T381A, F383A) Mutation

Reference Example 2-1: Preparation of pECCG117-ilvA(F383A)

In order to amplify ilvA (SEQ ID NO: 48), a gene encoding threonine dehydratase (SEQ ID NO: 47), BamHI restriction enzyme sites were inserted at both ends of the primers (SEQ ID NO: 49 and SEQ ID NO: 50) for amplification from the promoter region (about 300 bp upstream of the start codon) to the terminator region (about 100 bp downstream of the stop codon), based on the previously reported ilvA sequence introduced with F383A mutation (World J Microbiol Biotechnol (2015) 31:1369-1377). Additionally, primers (SEQ ID NO: 51 and SEQ ID NO: 52) were used for introducing the F383A mutation into ilvA. The primer sequences used herein are shown in Table 16 below.

TABLE 16

| SEQ ID NO: | Primer | Sequence (5'→3') |
|---|---|---|
| 49 | Primer 1 | ggatccGACTGAGCCTGGGCAACTGG |
| 50 | Primer 2 | ggatccCCGTCACCGACACCTCCACA |
| 51 | Primer 3 | ACATCACGCTGgcaGAGTACCTCAA |
| 52 | Primer 4 | TTGAGGTACTCtgcCAGCGTGATGT |

PCR was performed using the primer pairs of SEQ ID NOS: 49 and 52 and SEQ ID NOS: 50 and 51 based on the chromosome of the wild-type *Corynebacterium glutamicum* ATCC13032. The PCR was performed under conditions of denaturation at 95° C. for 5 minutes, followed by 30 cycles of denaturation at 95° C. for 30 seconds, annealing at 55° C. for 30 seconds, and polymerization at 72° C. for 1 minute and 30 seconds, and then polymerization at 72° C. for 5 minutes.

As a result, a DNA fragment (1460 bp) in the 5' upstream region and a DNA fragment (276 bp) in the 3' downstream region were obtained around the mutation of the ilvA gene.

PCR was carried out based on the two amplified DNA fragments as a template using the primers of SEQ ID NO: 49 and SEQ ID NO: 50.

As a result, the DNA fragment (1531 bp) including the mutation of ilvA gene, in which the 383rd phenylalanine was substituted with alanine, was amplified. The pECCG117 vector (Korean Patent No. 10-0057684) and the ilvA DNA fragment were treated with restriction enzyme BamHI, ligated using a DNA ligase, and cloned to obtain a plasmid, and the plasmid was named pECCG117-ilvA(F383A).

Reference Example 2-2: Additional Introduction of Random Mutation into pECCG117-ilvA(F383A)

In order to obtain a variant of the gene encoding L-threonine dehydratase, an ilvA mutant gene plasmid was prepared using a random mutagenesis kit (Agilent Technologies, USA). PCR was performed using the primers of SEQ ID NO: 49 and SEQ ID NO: 50 based on the chromosome of the ilvA(F383A) as a template. The PCR was performed under conditions of denaturation at 95° C. for 2 minutes, followed by 30 cycles of denaturation at 95° C. for 30 seconds, annealing at 55° C. for 30 seconds, and polymerization at 72° C. for 1 minute and 30 seconds, and then polymerization at 72° C. for 10 minutes.

As a result, the DNA fragment (1531 bp), which is an ilvA variant capable of encoding L-threonine dehydratase having a random mutation in addition to the mutation in which the 383rd phenylalanine was substituted with alanine, was amplified. The pECCG117 vector and the ilvA mutant DNA fragment were treated with restriction enzyme BamHI, ligated using a DNA ligase, and cloned to obtain a group of plasmids.

Reference Example 2-3: Preparation of CJILE-301 Strain pECCG117-ilvA(F383A) was introduced into the *Corynebacterium glutamicum*

ATCC13032 hom(R407H) strain, and the strain into which the resulting plasmid was introduced was named hom(R407H)/pECCG117-ilvA(F383A). In addition, the group of variant plasmids obtained in Reference 2-2 was introduced into the *Corynebacterium glutamicum* ATCC13032 hom(R407H) strain and plated onto a minimal medium, and the death rate was determined. As a result, the death rate was 70%, and the survived cells were inoculated and cultured in a seed medium. Finally, a mutant strain showing superior isoleucine producing ability compared to the control, ATCC13032 hom(R407H)/pECCG117-ilvA (F383A), was selected and named *Corynebacterium glutamicum* CJLE-301.

As a result of sequencing the ilvA gene by isolating the plasmid from the CJILE-301 strain, it was confirmed that the strain could encode the mutant protein, in which the 381st T was substituted with A, in addition to the mutation in which A, the 1141st nucleotide of the ilvA gene, was substituted to G, leading to the mutation in which the 383rd F of the ilvA protein was substituted with A, and this was represented by SEQ ID NO: 54.

Reference Example 2-4: Introduction of ilvA Variants (T381A, F383A)

Primers of SEQ ID NO: 49 and SEQ ID NO: 52 (Example 5-1, Table 16) were prepared in order to introduce the ilvA variants (T381A, F383A) into the wild-type strain.

In order to prepare a strain into which ilvA variants (T381A, F383A) were introduced, PCR was performed using the primers of SEQ ID NO: 49 and SEQ ID NO: 52 based on the plasmid DNA extracted from the CJILE-301 strain as a template.

PfuUltra™ high-reliability DNA polymerase (Stratagene) was used as the polymerase for the PCR reaction, and PCR was performed by repeating 28 cycles of denaturation at 95° C. for 30 seconds, annealing at 55° C. for 30 seconds, and polymerization at 72° C. for 2 minutes.

As a result, a gene fragment (1411 bp) including a terminator region of about 100 bp of the ilvA gene (1311 bp) was obtained.

The amplified product was purified using a PCR purification kit (QIAGEN) and used as an insert DNA fragment for the preparation of a vector. Meanwhile, after treating the purified amplified product with restriction enzyme SmaI, the ratio of the molar concentration (M) of the pDCM2 vector heat-treated at 65° C. for 20 minutes to the insert DNA fragment, the amplified product, was set to be 1:2, and the vector was cloned using an Infusion Cloning Kit (TaKaRa) according to the manufacturer's manual to thereby prepare the pDCM2-T381A_F383A vector for introducing the T381A and F383A mutations into the chromosome.

The thus-prepared vector was transformed into the *Corynebacterium glutamicum* ATCC13032 hom(R407H) by electroporation and subjected to secondary crossover, thereby obtaining a strain including the ilvA(T381A, F383A; SEQ ID NO: 53) mutation on the chromosome, and the strain was named CA10-3101.

The CA10-3101 strain was deposited at the Korean Culture Center of Microorganisms (KCCM), an International Depositary Authority, under the Budapest Treaty on May 27, 2020, with Accession No. KCCM12739P.

The KCCM12739P strain was inoculated into a 250 mL corner-baffled flask containing 25 mL of isoleucine production medium, and then cultured with shaking at 32° C. for 60 hours at 200 rpm to prepare L-isoleucine. The composition of the production medium used is as follows.

<Production Medium>

Glucose 10%, Yeast Extract 0.2%, $(NH_4)_2SO_4$ 1.6%, $KH_2PO_4$ 0.1%, $MgSO_4 \cdot 7H_2O$ 0.1%, $FeSO_4 \cdot 7H_2O$ 10 mg/L, $MnSO_4 \cdot H_2O$ 10 mg/L, Biotin 200 μg/L, pH 7.2

After completion of culture, the concentrations of L-isoleucine and L-threonine in the culture medium were measured using high-performance liquid chromatography (HPLC), and the results are shown in Table 17 below.

TABLE 17

| Name of Strain | L-Isoleucine (g/L) | L-Threonine (g/L) |
|---|---|---|
| ATCC13032 hom(R407H) | 0.0 | 3.8 |
| ATCC13032 hom(R407H) ilvA(WT) | 0.0 | 3.7 |
| CA10-3101(ATCC13032 hom(R407H) ilvA(T381A, F383A)) | 3.3 | 0.0 |

As shown in Table 17, the parent strain, *Corynebacterium glutamicum* ATCC13032 hom(R407H), was not able to produce L-isoleucine, but the ATCC13032 hom(R407H) ilvA(T381A, F383A) mutant strain was able to produce L-isoleucine at a concentration of 3.9 g/L, thereby confirming that the productivity of L-isoleucine was significantly increased compared to the parent strain.

Based on the result, it was confirmed that the ilvA (T381A, F383A) mutation is an effective mutation for increasing isoleucine production.

Reference Example 3: Confirmation of Leucine Production of IeuA(P247C, R558H, G561D)

Reference Example 3-1. Preparation of CJL-8100 Strain

Specifically, the vector pDCM2-leuA(R558H, G561D) containing the IeuA gene mutation disclosed in KR 10-2018-0077008 A was transformed into the *Corynebacterium glutamicum* ATCC13032 by electroporation, and a strain into which the vector was inserted into the chromosome by recombination of the homologous sequence was selected in a medium containing 25 mg/L kanamycin. The selected primary strain was again subjected to secondary crossover, and a strain into which the IeuA gene mutation was introduced were selected. The introduction of the mutation into the finally transformed strain was confirmed by performing PCR using the primers of SEQ ID NO: 55 and SEQ ID NO: 56 under conditions of denaturation at 94° C. for 5 minutes, followed by 30 cycles of denaturation at 94° C. for 30 seconds, annealing at 55° C. for 30 seconds, and polymerization at 72° C. for 1 minute and 30 seconds, and then polymerization at 72° C. for 5 minutes and analyzing the nucleotide sequences, thereby confirming the introduction of R558H and G561D mutations. The ATCC13032_leuA_(R558H, G561D) strain transformed with the pDCM2-leuA (R558H, G561D) vector was named "CJL-8100".

The primer sequences used in Reference Example 3 below are shown in Table 18.

TABLE 18

| SEQ ID NO: | Sequence (5'→3') |
|---|---|
| SEQ ID NO: 55 | AACACGACCGGCATCCCGTCGC |
| SEQ ID NO: 56 | AAATCATTTGAGAAAACTCGAGG |
| SEQ ID NO: 57 | GTGAATTCGAGCTCGGTACCCAA ATCATTTGAGAAAACTCGAGGC |
| SEQ ID NO: 58 | GGTGATCATCTCAACGGTGGAAC ACAGGTTGATGATCATTGGGTT |
| SEQ ID NO: 59 | AACCCAATGATCATCAACCTGTG TTCCACCGTTGAGATGATCACC |
| SEQ ID NO: 60 | GGTCGACTCTAGAGGATCCCCAA GAAGGCAACATCGGACAGC |
| SEQ ID NO: 61 | ATCCATTCAATGGAGTCTGCG |

Reference Example 3-2. Preparation of Insertion Vector Containing IeuA Mutation A vector was prepared for introducing the P247C mutation into CJL-8100, an L-leucine-producing strain in which two mutations (R558H, G561 D) were introduced into LeuA.

PCR was performed using the primer pairs of SEQ ID NOS: 57 and 58 or SEQ ID NOS: 59 and 60 based on the chromosome of the CJL-8100 strain. The PCR was performed under conditions of denaturation at 94° C. for 5 minutes, followed by 30 cycles of denaturation at 94° C. for 30 seconds, annealing at 55° C. for 30 seconds, and polymerization at 72° C. for 1 minute and 30 seconds, and then polymerization at 72° C. for 5 minutes. The resulting PCR products were cloned by fusion of the homologous sequence of the terminal 15 bases between the DNA fragments using the linear pDCM2 vector digested with Smal restriction enzyme and the In-Fusion enzyme to prepare the pDCM2-leuA(P247C, R558H, G561D) vector containing the IeuA mutation encoding the LeuA mutant, in which arginine, the 558th amino acid, was substituted with histidine, and glycine, the 561st amino acid, was substituted with aspartic acid, and for substituting proline (Pro), the 247th amino acid, with cysteine (Cys).

Reference Example 3-3. Introduction of LeuA Variant (P247C) into CJL-8100 Strain and Evaluation Thereof The L-leucine-producing strain CJL-8100 was transformed into the pDCM2-leuA(P247C, R558H, G561D) vector prepared in Reference Example 3-2, and a strain into which the vector was inserted into the chromosome by recombination of the homologous sequence was selected in a medium containing 25 mg/L kanamycin. The selected primary strain was again subjected to secondary crossover, and a strain into which the mutation of the target gene was introduced was selected. The introduction of the mutation of the IeuA gene into the finally transformed strain was confirmed by performing PCR using the primers of SEQ ID NO: 55 and SEQ ID NO: 61 under conditions of denaturation at 94° C. for 5 minutes, followed by 30 cycles of denaturation at 94° C. for 30 seconds, annealing at 55° C. for 30 seconds, and polymerization at 72° C. for 1 minute and 30 seconds, and then polymerization at 72° C. for 5 minutes and analyzing the nucleotide sequences. As a result of the analysis, it was confirmed that the IeuA mutation encoding the LeuA variants (P247C, R558H, G561D) in which G, the 1673rd nucleotide of the IeuA gene in the chromosome of the strain, was substituted with A, GC, which were the 1682nd and 1683rd nucleotides, were substituted with AT, CC, which were the 739th and 740th nucleotides, were substituted with TG, arginine, the 558th amino acid of the LeuA protein, was substituted with histidine, glycine, the 561st amino acid was substituted with aspartic acid, and proline (Pro), the 247th amino acid was substituted with cysteine (Cys).

The thus-prepared CJL8100_IeuA_P247C was named "CA13-8105" and deposited at the Korean Culture Center of Microorganisms (KCCM), an International Depositary Authority, under the Budapest Treaty on Apr. 29, 2020, with Accession No. KCCM12709P.

The amino acid sequence of the LeuA variant (P247C, R558H, G561D) including the above three mutations and the nucleotide sequence of the IeuA variant encoding the same are represented by SEQ ID NO: 62 and SEQ ID NO: 63, respectively.

The L-leucine producing ability of ATCC13032, the thus-produced CJL-8100, and CA13-8105 strains was evaluated. Specifically, flask culture was carried out in the same manner as in Example 2-1, and after completion of the culture, the L-leucine production of the parent strain and the mutant strains was measured using HPLC, and the results are shown in Table 19.

TABLE 19

| Name of Strain | L-Leucine (g/L) |
|---|---|
| ATCC13032 | 0.87 |
| ATCC13032_leuA_(R558H, G561D):CJL-8100 | 2.71 |
| CJL8100_leuA_P247C:CA13-8105 | 3.52 |

As shown in Table 19, the *Corynebacterium glutamicum* CJL8100, an L-leucine-producing strain, showed an improved L-leucine producing ability by about 130% compared to the parent strain ATCC13032. Additionally, the CA13-8105 strain, into which the leuA_P247C mutation was further introduced in the CJL8100 strain, showed an improved L-leucine producing ability by about 150% compared to the parent strain CJL8100.

Based on the result, it was confirmed that the leuA (R558H, G561D, P247C) mutation is an effective mutation for increasing leucine production.

Those of ordinary skill in the art will recognize that the present application may be embodied in other specific forms without departing from its spirit or essential characteristics. The described embodiments are to be considered in all respects only as illustrative and not restrictive. The scope of the present application is therefore indicated by the appended claims rather than by the foregoing description. All changes which come within the meaning and range of equivalency of the claims are to be embraced within the scope of the present application.

The invention claimed is:

1. An aroG aldolase (phospho-2-dehydro-3-deoxyheptonate aldolase) variant, in which at least one amino acid selected from the group consisting of the amino acids corresponding to positions 217, 310, 403, and 462 from the N-terminus in the amino acid sequence of SEQ ID NO: 1 is substituted with another amino acid, wherein the aroG aldolase variant has a sequence identity of 90% or more with SEQ ID NO: 1.

2. The aroG aldolase variant of claim 1, wherein the substitution with another amino acid is a substitution with a nonpolar amino acid or an amino acid selected from the group consisting of glycine, alanine, serine, threonine, cysteine, valine, leucine, isoleucine, and proline.

3. The aroG aldolase variant of claim 1, wherein the another amino acid is alanine (Ala).

4. The aroG aldolase variant of claim 1, wherein the aroG aldolase variant has a sequence identity of 99% or more with SEQ ID NO: 3, SEQ ID NO: 5, SEQ ID NO: 7, or SEQ ID NO: 9.

5. The aroG aldolase variant of claim 1, wherein the aroG aldolase variant has a weakened adolase activity compared to the aroG aldolase of SEQ ID NO: 1.

6. A polynucleotide encoding the aroG aldolase variant of claim 1.

7. A vector containing the polynucleotide of claim 6.

8. A microorganism of the genus *Corynebacterium*, comprising one or more of the aroG aldolase variant of claim 1, a polynucleotide encoding the aroG aldolase variant; and a vector containing the polynucleotide.

9. The microorganism of the genus *Corynebacterium* of claim 8, wherein the microorganism of the genus *Corynebacterium* is *Corynebacterium glutamicum.*

10. A method for producing branched-chain amino acids, comprising culturing the microorganism of the genus *Corynebacterium* of claim 8 in a medium.

11. The method of claim 10, wherein the method further comprises recovering branched-chain amino acids from the microorganism or the medium.

12. The method of claim 11, wherein the branched-chain amino acids comprise one or more selected from the group consisting of L-leucine, L-isoleucine, and L-valine.

13. The aroG aldolase variant of claim 1, wherein the variant has a sequence identity of 95% or more with SEQ ID NO: 1.

14. The aroG aldolase variant of claim 1, wherein the variant has a sequence identity of 99% or more with SEQ ID NO: 1.

15. The aroG aldolase variant of claim 1, wherein the amino acid corresponding to position 217 from the N-terminus in the amino acid sequence of SEQ ID NO: 1 is substituted with another amino acid.

16. The aroG aldolase variant of claim 1, wherein the amino acid corresponding to position 310 from the N-terminus in the amino acid sequence of SEQ ID NO: 1 is substituted with another amino acid.

17. The aroG aldolase variant of claim 1, wherein the amino acid corresponding to position 403 from the N-terminus in the amino acid sequence of SEQ ID NO: 1 is substituted with another amino acid.

18. The aroG aldolase variant of claim 1, wherein the amino acid corresponding to position 462 from the N-terminus in the amino acid sequence of SEQ ID NO: 1 is substituted with another amino acid.

19. The aroG aldolase variant of claim 1, wherein the aroG aldolase variant has a sequence identity of 99% or more with SEQ ID NO: 23.

20. The aroG aldolase variant of claim 1, wherein the aroG aldolase variant has a sequence identity of 99% or more with SEQ ID NO: 25.

* * * * *

SEQUENCE LISTING

```
<160> NUMBER OF SEQ ID NOS: 63

<210> SEQ ID NO 1
<211> LENGTH: 466
<212> TYPE: PRT
<213> ORGANISM: Unknown
<220> FEATURE:
<223> OTHER INFORMATION: aroG_WT

<400> SEQUENCE: 1

Met Asn Arg Gly Val Ser Trp Thr Val Asp Ile Pro Lys Glu Val Leu
1               5                   10                  15

Pro Asp Leu Pro Pro Leu Pro Glu Gly Met Gln Gln Gln Phe Glu Asp
            20                  25                  30

Thr Ile Ser Arg Asp Ala Lys Gln Gln Pro Thr Trp Asp Arg Ala Gln
        35                  40                  45

Ala Glu Asn Val Arg Lys Ile Leu Glu Ser Val Pro Pro Ile Val Val
    50                  55                  60

Ala Pro Glu Val Leu Glu Leu Lys Gln Lys Leu Ala Asp Val Ala Asn
65                  70                  75                  80

Gly Lys Ala Phe Leu Leu Gln Gly Gly Asp Cys Ala Glu Thr Phe Glu
                85                  90                  95

Ser Asn Thr Glu Pro His Ile Arg Ala Asn Val Lys Thr Leu Leu Gln
            100                 105                 110

Met Ala Val Val Leu Thr Tyr Gly Ala Ser Thr Pro Val Ile Lys Met
        115                 120                 125

Ala Arg Ile Ala Gly Gln Tyr Ala Lys Pro Arg Ser Ser Asp Leu Asp
    130                 135                 140

Gly Asn Gly Leu Pro Asn Tyr Arg Gly Asp Ile Val Asn Gly Val Glu
```

145 150 155 160

Ala Thr Pro Glu Ala Arg Arg His Asp Pro Ala Arg Met Ile Arg Ala
165 170 175

Tyr Ala Asn Ala Ser Ala Ala Met Asn Leu Val Arg Ala Leu Thr Ser
180 185 190

Ser Gly Thr Ala Asp Leu Tyr Arg Leu Ser Glu Trp Asn Arg Glu Phe
195 200 205

Val Ala Asn Ser Pro Ala Gly Ala Arg Tyr Glu Ala Leu Ala Arg Glu
210 215 220

Ile Asp Ser Gly Leu Arg Phe Met Glu Ala Cys Gly Val Ser Asp Glu
225 230 235 240

Ser Leu Arg Ala Ala Asp Ile Tyr Cys Ser His Glu Ala Leu Leu Val
245 250 255

Asp Tyr Glu Arg Ser Met Leu Arg Leu Ala Thr Asp Glu Glu Gly Asn
260 265 270

Glu Glu Leu Tyr Asp Leu Ser Ala His Gln Leu Trp Ile Gly Glu Arg
275 280 285

Thr Arg Gly Met Asp Asp Phe His Val Asn Phe Ala Ser Met Ile Ser
290 295 300

Asn Pro Ile Gly Ile Lys Ile Gly Pro Gly Ile Thr Pro Glu Glu Ala
305 310 315 320

Val Ala Tyr Ala Asp Lys Leu Asp Pro Asn Phe Glu Pro Gly Arg Leu
325 330 335

Thr Ile Val Ala Arg Met Gly His Asp Lys Val Arg Ser Val Leu Pro
340 345 350

Gly Val Ile Gln Ala Val Glu Ala Ser Gly His Lys Val Ile Trp Gln
355 360 365

Ser Asp Pro Met His Gly Asn Thr Phe Thr Ala Ser Asn Gly Tyr Lys
370 375 380

Thr Arg His Phe Asp Lys Val Ile Asp Glu Val Gln Gly Phe Phe Glu
385 390 395 400

Val His Arg Ala Leu Gly Thr His Pro Gly Gly Ile His Ile Glu Phe
405 410 415

Thr Gly Glu Asp Val Thr Glu Cys Leu Gly Gly Ala Glu Asp Ile Thr
420 425 430

Asp Val Asp Leu Pro Gly Arg Tyr Glu Ser Ala Cys Asp Pro Arg Leu
435 440 445

Asn Thr Gln Gln Ser Leu Glu Leu Ala Phe Leu Val Ala Glu Met Leu
450 455 460

Arg Asn
465

<210> SEQ ID NO 2
<211> LENGTH: 1401
<212> TYPE: DNA
<213> ORGANISM: Unknown
<220> FEATURE:
<223> OTHER INFORMATION: aroG_WT

<400> SEQUENCE: 2
atgaataggg gtgtgagttg gacagttgat atccctaaag aagttctccc tgatttgcca 60
ccattgccag aaggcatgca gcagcagttc gaggacacca tttcccgtga cgctaagcag 120
caacctacgt gggatcgtgc acaggcagaa aacgtgcgca agatccttga gtcggttcct 180
ccaatcgttg ttgcccctga ggtacttgag ctgaagcaga agcttgctga tgttgccaac 240

```
ggtaaggcct tcctcttgca gggtggtgac tgtgcggaaa ctttcgagtc aaacactgag    300

ccgcacattc gcgccaacgt aaagactctg ctgcagatgg cagttgtttt gacctacggt    360

gcatccactc ctgtgatcaa gatggctcgt attgctggtc agtacgcaaa gcctcgctct    420

tctgatctgg atggaaatgg tctgccaaac taccgtggcg atatcgtcaa cggtgtggag    480

gcaaccccag aggctcgtcg ccacgatcct gcccgcatga tccgtgctta cgctaacgct    540

tctgctgcga tgaacttggt gcgcgcgctc accagctctg gcaccgctga tctttaccgt    600

ctcagcgagt ggaaccgcga gttcgttgcg aactccccag ctggtgcacg ctacgaggct    660

cttgctcgtg agatcgactc cggtctgcgc ttcatggaag catgtggcgt gtccgatgag    720

tccctgcgtg ctgcagatat ctactgctcc cacgaggctt tgctggtgga ttacgagcgt    780

tccatgctgc gtcttgcaac cgatgaggaa ggcaacgagg aactttacga tctttcagct    840

caccagctgt ggatcggcga gcgcacccgt ggcatggatg atttccatgt gaacttcgca    900

tccatgatct ctaacccaat cggcatcaag attggtcctg gtatcacccc tgaagaggct    960

gttgcatacg ctgacaagct cgatccgaac ttcgagcctg gccgtttgac catcgttgct   1020

cgcatgggcc acgacaaggt tcgctccgta cttcctggtg ttatccaggc tgttgaggca   1080

tccggacaca aggttatttg gcagtccgat ccgatgcacg gcaacacttt caccgcatcc   1140

aatggctaca agacccgtca cttcgacaag gttatcgatg aggtccaggg cttcttcgag   1200

gtccaccgcg cattgggcac ccacccaggc ggaatccaca ttgagttcac tggtgaagat   1260

gtcaccgagt gcctcggtgg cgctgaagac atcaccgatg ttgatctgcc aggccgctac   1320

gagtccgcat gcgatcctcg cctgaacact cagcagtctt tggagttggc tttcctcgtt   1380

gcagaaatgc tgcgtaacta a                                             1401
```

```
<210> SEQ ID NO 3
<211> LENGTH: 466
<212> TYPE: PRT
<213> ORGANISM: Artificial Sequence
<220> FEATURE:
<223> OTHER INFORMATION: aroG_R217A

<400> SEQUENCE: 3

Met Asn Arg Gly Val Ser Trp Thr Val Asp Ile Pro Lys Glu Val Leu
1               5                   10                  15

Pro Asp Leu Pro Pro Leu Pro Glu Gly Met Gln Gln Gln Phe Glu Asp
            20                  25                  30

Thr Ile Ser Arg Asp Ala Lys Gln Gln Pro Thr Trp Asp Arg Ala Gln
        35                  40                  45

Ala Glu Asn Val Arg Lys Ile Leu Glu Ser Val Pro Pro Ile Val Val
    50                  55                  60

Ala Pro Glu Val Leu Glu Leu Lys Gln Lys Leu Ala Asp Val Ala Asn
65                  70                  75                  80

Gly Lys Ala Phe Leu Leu Gln Gly Gly Asp Cys Ala Glu Thr Phe Glu
                85                  90                  95

Ser Asn Thr Glu Pro His Ile Arg Ala Asn Val Lys Thr Leu Leu Gln
            100                 105                 110

Met Ala Val Val Leu Thr Tyr Gly Ala Ser Thr Pro Val Ile Lys Met
        115                 120                 125

Ala Arg Ile Ala Gly Gln Tyr Ala Lys Pro Arg Ser Ser Asp Leu Asp
    130                 135                 140

Gly Asn Gly Leu Pro Asn Tyr Arg Gly Asp Ile Val Asn Gly Val Glu
```

-continued 145 150 155 160

Ala Thr Pro Glu Ala Arg Arg His Asp Pro Ala Arg Met Ile Arg Ala
165 170 175

Tyr Ala Asn Ala Ser Ala Ala Met Asn Leu Val Arg Ala Leu Thr Ser
180 185 190

Ser Gly Thr Ala Asp Leu Tyr Arg Leu Ser Glu Trp Asn Arg Glu Phe
195 200 205

Val Ala Asn Ser Pro Ala Gly Ala Ala Tyr Glu Ala Leu Ala Arg Glu
210 215 220

Ile Asp Ser Gly Leu Arg Phe Met Glu Ala Cys Gly Val Ser Asp Glu
225 230 235 240

Ser Leu Arg Ala Ala Asp Ile Tyr Cys Ser His Glu Ala Leu Leu Val
245 250 255

Asp Tyr Glu Arg Ser Met Leu Arg Leu Ala Thr Asp Glu Glu Gly Asn
260 265 270

Glu Glu Leu Tyr Asp Leu Ser Ala His Gln Leu Trp Ile Gly Glu Arg
275 280 285

Thr Arg Gly Met Asp Asp Phe His Val Asn Phe Ala Ser Met Ile Ser
290 295 300

Asn Pro Ile Gly Ile Lys Ile Gly Pro Gly Ile Thr Pro Glu Glu Ala
305 310 315 320

Val Ala Tyr Ala Asp Lys Leu Asp Pro Asn Phe Glu Pro Gly Arg Leu
325 330 335

Thr Ile Val Ala Arg Met Gly His Asp Lys Val Arg Ser Val Leu Pro
340 345 350

Gly Val Ile Gln Ala Val Glu Ala Ser Gly His Lys Val Ile Trp Gln
355 360 365

Ser Asp Pro Met His Gly Asn Thr Phe Thr Ala Ser Asn Gly Tyr Lys
370 375 380

Thr Arg His Phe Asp Lys Val Ile Asp Glu Val Gln Gly Phe Phe Glu
385 390 395 400

Val His Arg Ala Leu Gly Thr His Pro Gly Gly Ile His Ile Glu Phe
405 410 415

Thr Gly Glu Asp Val Thr Glu Cys Leu Gly Gly Ala Glu Asp Ile Thr
420 425 430

Asp Val Asp Leu Pro Gly Arg Tyr Glu Ser Ala Cys Asp Pro Arg Leu
435 440 445

Asn Thr Gln Gln Ser Leu Glu Leu Ala Phe Leu Val Ala Glu Met Leu
450 455 460

Arg Asn
465

<210> SEQ ID NO 4
<211> LENGTH: 1401
<212> TYPE: DNA
<213> ORGANISM: Artificial Sequence
<220> FEATURE:
<223> OTHER INFORMATION: aroG_R217A_nt

<400> SEQUENCE: 4
atgaataggg gtgtgagttg gacagttgat atccctaaag aagttctccc tgatttgcca 60
ccattgccag aaggcatgca gcagcagttc gaggacacca tttcccgtga cgctaagcag 120
caacctacgt gggatcgtgc acaggcagaa aacgtgcgca agatccttga gtcggttcct 180
ccaatcgttg ttgcccctga ggtacttgag ctgaagcaga agcttgctga tgttgccaac 240

-continued

```
ggtaaggcct tcctcttgca gggtggtgac tgtgcggaaa ctttcgagtc aaacactgag    300

ccgcacattc gcgccaacgt aaagactctg ctgcagatgg cagttgtttt gacctacggt    360

gcatccactc ctgtgatcaa gatggctcgt attgctggtc agtacgcaaa gcctcgctct    420

tctgatctgg atggaaatgg tctgccaaac taccgtggcg atatcgtcaa cggtgtggag    480

gcaaccccag aggctcgtcg ccacgatcct gcccgcatga tccgtgctta cgctaacgct    540

tctgctgcga tgaacttggt gcgcgcgctc accagctctg gcaccgctga tctttaccgt    600

ctcagcgagt ggaaccgcga gttcgttgcg aactccccag ctggtgcagc gtacgaggct    660

cttgctcgtg agatcgactc cggtctgcgc ttcatggaag catgtggcgt gtccgatgag    720

tccctgcgtg ctgcagatat ctactgctcc cacgaggctt tgctggtgga ttacgagcgt    780

tccatgctgc gtcttgcaac cgatgaggaa ggcaacgagg aactttacga tctttcagct    840

caccagctgt ggatcggcga gcgcacccgt ggcatggatg atttccatgt gaacttcgca    900

tccatgatct ctaacccaat cggcatcaag attggtcctg gtatcacccc tgaagaggct    960

gttgcatacg ctgacaagct cgatccgaac ttcgagcctg gccgtttgac catcgttgct   1020

cgcatgggcc acgacaaggt tcgctccgta cttcctggtg ttatccaggc tgttgaggca   1080

tccggacaca aggttatttg gcagtccgat ccgatgcacg gcaacacttt caccgcatcc   1140

aatggctaca agacccgtca cttcgacaag gttatcgatg aggtccaggg cttcttcgag   1200

gtccaccgcg cattgggcac ccacccaggc ggaatccaca ttgagttcac tggtgaagat   1260

gtcaccgagt gcctcggtgg cgctgaagac atcaccgatg ttgatctgcc aggccgctac   1320

gagtccgcat gcgatcctcg cctgaacact cagcagtctt tggagttggc tttcctcgtt   1380

gcagaaatgc tgcgtaacta a                                             1401
```

```
<210> SEQ ID NO 5
<211> LENGTH: 466
<212> TYPE: PRT
<213> ORGANISM: Artificial Sequence
<220> FEATURE:
<223> OTHER INFORMATION: aroG_K310A

<400> SEQUENCE: 5

Met Asn Arg Gly Val Ser Trp Thr Val Asp Ile Pro Lys Glu Val Leu
1               5                   10                  15

Pro Asp Leu Pro Pro Leu Pro Glu Gly Met Gln Gln Gln Phe Glu Asp
            20                  25                  30

Thr Ile Ser Arg Asp Ala Lys Gln Gln Pro Thr Trp Asp Arg Ala Gln
        35                  40                  45

Ala Glu Asn Val Arg Lys Ile Leu Glu Ser Val Pro Pro Ile Val Val
    50                  55                  60

Ala Pro Glu Val Leu Glu Leu Lys Gln Lys Leu Ala Asp Val Ala Asn
65                  70                  75                  80

Gly Lys Ala Phe Leu Leu Gln Gly Gly Asp Cys Ala Glu Thr Phe Glu
                85                  90                  95

Ser Asn Thr Glu Pro His Ile Arg Ala Asn Val Lys Thr Leu Leu Gln
            100                 105                 110

Met Ala Val Val Leu Thr Tyr Gly Ala Ser Thr Pro Val Ile Lys Met
        115                 120                 125

Ala Arg Ile Ala Gly Gln Tyr Ala Lys Pro Arg Ser Ser Asp Leu Asp
    130                 135                 140

Gly Asn Gly Leu Pro Asn Tyr Arg Gly Asp Ile Val Asn Gly Val Glu
```

145 150 155 160

Ala Thr Pro Glu Ala Arg Arg His Asp Pro Ala Arg Met Ile Arg Ala
165 170 175

Tyr Ala Asn Ala Ser Ala Ala Met Asn Leu Val Arg Ala Leu Thr Ser
180 185 190

Ser Gly Thr Ala Asp Leu Tyr Arg Leu Ser Glu Trp Asn Arg Glu Phe
195 200 205

Val Ala Asn Ser Pro Ala Gly Ala Arg Tyr Glu Ala Leu Ala Arg Glu
210 215 220

Ile Asp Ser Gly Leu Arg Phe Met Glu Ala Cys Gly Val Ser Asp Glu
225 230 235 240

Ser Leu Arg Ala Ala Asp Ile Tyr Cys Ser His Glu Ala Leu Leu Val
245 250 255

Asp Tyr Glu Arg Ser Met Leu Arg Leu Ala Thr Asp Glu Glu Gly Asn
260 265 270

Glu Glu Leu Tyr Asp Leu Ser Ala His Gln Leu Trp Ile Gly Glu Arg
275 280 285

Thr Arg Gly Met Asp Asp Phe His Val Asn Phe Ala Ser Met Ile Ser
290 295 300

Asn Pro Ile Gly Ile Ala Ile Gly Pro Gly Ile Thr Pro Glu Glu Ala
305 310 315 320

Val Ala Tyr Ala Asp Lys Leu Asp Pro Asn Phe Glu Pro Gly Arg Leu
325 330 335

Thr Ile Val Ala Arg Met Gly His Asp Lys Val Arg Ser Val Leu Pro
340 345 350

Gly Val Ile Gln Ala Val Glu Ala Ser Gly His Lys Val Ile Trp Gln
355 360 365

Ser Asp Pro Met His Gly Asn Thr Phe Thr Ala Ser Asn Gly Tyr Lys
370 375 380

Thr Arg His Phe Asp Lys Val Ile Asp Glu Val Gln Gly Phe Phe Glu
385 390 395 400

Val His Arg Ala Leu Gly Thr His Pro Gly Gly Ile His Ile Glu Phe
405 410 415

Thr Gly Glu Asp Val Thr Glu Cys Leu Gly Gly Ala Glu Asp Ile Thr
420 425 430

Asp Val Asp Leu Pro Gly Arg Tyr Glu Ser Ala Cys Asp Pro Arg Leu
435 440 445

Asn Thr Gln Gln Ser Leu Glu Leu Ala Phe Leu Val Ala Glu Met Leu
450 455 460

Arg Asn
465

<210> SEQ ID NO 6
<211> LENGTH: 1401
<212> TYPE: DNA
<213> ORGANISM: Artificial Sequence
<220> FEATURE:
<223> OTHER INFORMATION: aroG_K310A_nt

<400> SEQUENCE: 6
atgaataggg gtgtgagttg gacagttgat atccctaaag aagttctccc tgatttgcca 60
ccattgccag aaggcatgca gcagcagttc gaggacacca tttcccgtga cgctaagcag 120
caacctacgt gggatcgtgc acaggcagaa aacgtgcgca agatccttga gtcggttcct 180
ccaatcgttg ttgcccctga ggtacttgag ctgaagcaga agcttgctga tgttgccaac 240

```
ggtaaggcct tcctcttgca gggtggtgac tgtgcggaaa ctttcgagtc aaacactgag    300

ccgcacattc gcgccaacgt aaagactctg ctgcagatgg cagttgtttt gacctacggt    360

gcatccactc ctgtgatcaa gatggctcgt attgctggtc agtacgcaaa gcctcgctct    420

tctgatctgg atggaaatgg tctgccaaac taccgtggcg atatcgtcaa cggtgtggag    480

gcaaccccag aggctcgtcg ccacgatcct gcccgcatga tccgtgctta cgctaacgct    540

tctgctgcga tgaacttggt gcgcgcgctc accagctctg gcaccgctga tctttaccgt    600

ctcagcgagt ggaaccgcga gttcgttgcg aactccccag ctggtgcacg ctacgaggct    660

cttgctcgtg agatcgactc cggtctgcgc ttcatggaag catgtggcgt gtccgatgag    720

tccctgcgtg ctgcagatat ctactgctcc cacgaggctt tgctggtgga ttacgagcgt    780

tccatgctgc gtcttgcaac cgatgaggaa ggcaacgagg aactttacga tctttcagct    840

caccagctgt ggatcggcga gcgcacccgt ggcatggatg atttccatgt gaacttcgca    900

tccatgatct ctaacccaat cggcatcgcg attggtcctg gtatcacccc tgaagaggct    960

gttgcatacg ctgacaagct cgatccgaac ttcgagcctg gccgtttgac catcgttgct   1020

cgcatgggcc acgacaaggt tcgctccgta cttcctggtg ttatccaggc tgttgaggca   1080

tccggacaca aggttatttg gcagtccgat ccgatgcacg gcaacacttt caccgcatcc   1140

aatggctaca agacccgtca cttcgacaag gttatcgatg aggtccaggg cttcttcgag   1200

gtccaccgcg cattgggcac ccacccaggc ggaatccaca ttgagttcac tggtgaagat   1260

gtcaccgagt gcctcggtgg cgctgaagac atcaccgatg ttgatctgcc aggccgctac   1320

gagtccgcat gcgatcctcg cctgaacact cagcagtctt tggagttggc tttcctcgtt   1380

gcagaaatgc tgcgtaacta a                                             1401
```

<210> SEQ ID NO 7
<211> LENGTH: 466
<212> TYPE: PRT
<213> ORGANISM: Artificial Sequence
<220> FEATURE:
<223> OTHER INFORMATION: aroG_R403A

<400> SEQUENCE: 7

```
Met Asn Arg Gly Val Ser Trp Thr Val Asp Ile Pro Lys Glu Val Leu
1               5                   10                  15

Pro Asp Leu Pro Pro Leu Pro Glu Gly Met Gln Gln Gln Phe Glu Asp
            20                  25                  30

Thr Ile Ser Arg Asp Ala Lys Gln Gln Pro Thr Trp Asp Arg Ala Gln
        35                  40                  45

Ala Glu Asn Val Arg Lys Ile Leu Glu Ser Val Pro Pro Ile Val Val
    50                  55                  60

Ala Pro Glu Val Leu Glu Leu Lys Gln Lys Leu Ala Asp Val Ala Asn
65                  70                  75                  80

Gly Lys Ala Phe Leu Leu Gln Gly Gly Asp Cys Ala Glu Thr Phe Glu
                85                  90                  95

Ser Asn Thr Glu Pro His Ile Arg Ala Asn Val Lys Thr Leu Leu Gln
            100                 105                 110

Met Ala Val Val Leu Thr Tyr Gly Ala Ser Thr Pro Val Ile Lys Met
        115                 120                 125

Ala Arg Ile Ala Gly Gln Tyr Ala Lys Pro Arg Ser Ser Asp Leu Asp
    130                 135                 140

Gly Asn Gly Leu Pro Asn Tyr Arg Gly Asp Ile Val Asn Gly Val Glu
```

```
145                 150                 155                 160

Ala Thr Pro Glu Ala Arg Arg His Asp Pro Ala Arg Met Ile Arg Ala
                165                 170                 175

Tyr Ala Asn Ala Ser Ala Ala Met Asn Leu Val Arg Ala Leu Thr Ser
            180                 185                 190

Ser Gly Thr Ala Asp Leu Tyr Arg Leu Ser Glu Trp Asn Arg Glu Phe
        195                 200                 205

Val Ala Asn Ser Pro Ala Gly Ala Arg Tyr Glu Ala Leu Ala Arg Glu
    210                 215                 220

Ile Asp Ser Gly Leu Arg Phe Met Glu Ala Cys Gly Val Ser Asp Glu
225                 230                 235                 240

Ser Leu Arg Ala Ala Asp Ile Tyr Cys Ser His Glu Ala Leu Leu Val
                245                 250                 255

Asp Tyr Glu Arg Ser Met Leu Arg Leu Ala Thr Asp Glu Glu Gly Asn
            260                 265                 270

Glu Glu Leu Tyr Asp Leu Ser Ala His Gln Leu Trp Ile Gly Glu Arg
        275                 280                 285

Thr Arg Gly Met Asp Asp Phe His Val Asn Phe Ala Ser Met Ile Ser
    290                 295                 300

Asn Pro Ile Gly Ile Lys Ile Gly Pro Gly Ile Thr Pro Glu Glu Ala
305                 310                 315                 320

Val Ala Tyr Ala Asp Lys Leu Asp Pro Asn Phe Glu Pro Gly Arg Leu
                325                 330                 335

Thr Ile Val Ala Arg Met Gly His Asp Lys Val Arg Ser Val Leu Pro
            340                 345                 350

Gly Val Ile Gln Ala Val Glu Ala Ser Gly His Lys Val Ile Trp Gln
        355                 360                 365

Ser Asp Pro Met His Gly Asn Thr Phe Thr Ala Ser Asn Gly Tyr Lys
    370                 375                 380

Thr Arg His Phe Asp Lys Val Ile Asp Glu Val Gln Gly Phe Phe Glu
385                 390                 395                 400

Val His Ala Ala Leu Gly Thr His Pro Gly Gly Ile His Ile Glu Phe
                405                 410                 415

Thr Gly Glu Asp Val Thr Glu Cys Leu Gly Gly Ala Glu Asp Ile Thr
            420                 425                 430

Asp Val Asp Leu Pro Gly Arg Tyr Glu Ser Ala Cys Asp Pro Arg Leu
        435                 440                 445

Asn Thr Gln Gln Ser Leu Glu Leu Ala Phe Leu Val Ala Glu Met Leu
    450                 455                 460

Arg Asn
465


<210> SEQ ID NO 8
<211> LENGTH: 1401
<212> TYPE: DNA
<213> ORGANISM: Artificial Sequence
<220> FEATURE:
<223> OTHER INFORMATION: aroG_R403A_nt

<400> SEQUENCE: 8

atgaataggg gtgtgagttg gacagttgat atccctaaag aagttctccc tgatttgcca      60

ccattgccag aaggcatgca gcagcagttc gaggacacca tttcccgtga cgctaagcag     120

caacctacgt gggatcgtgc acaggcagaa aacgtgcgca agatccttga gtcggttcct     180

ccaatcgttg ttgcccctga ggtacttgag ctgaagcaga agcttgctga tgttgccaac     240
```

```
ggtaaggcct tcctcttgca gggtggtgac tgtgcggaaa ctttcgagtc aaacactgag    300

ccgcacattc gcgccaacgt aaagactctg ctgcagatgg cagttgtttt gacctacggt    360

gcatccactc ctgtgatcaa gatggctcgt attgctggtc agtacgcaaa gcctcgctct    420

tctgatctgg atggaaatgg tctgccaaac taccgtggcg atatcgtcaa cggtgtggag    480

gcaaccccag aggctcgtcg ccacgatcct gcccgcatga tccgtgctta cgctaacgct    540

tctgctgcga tgaacttggt gcgcgcgctc accagctctg gcaccgctga tctttaccgt    600

ctcagcgagt ggaaccgcga gttcgttgcg aactccccag ctggtgcacg ctacgaggct    660

cttgctcgtg agatcgactc cggtctgcgc ttcatggaag catgtggcgt gtccgatgag    720

tccctgcgtg ctgcagatat ctactgctcc cacgaggctt tgctggtgga ttacgagcgt    780

tccatgctgc gtcttgcaac cgatgaggaa ggcaacgagg aactttacga tctttcagct    840

caccagctgt ggatcggcga gcgcacccgt ggcatggatg atttccatgt gaacttcgca    900

tccatgatct ctaacccaat cggcatcaag attggtcctg gtatcacccc tgaagaggct    960

gttgcatacg ctgacaagct cgatccgaac ttcgagcctg gccgtttgac catcgttgct   1020

cgcatgggcc acgacaaggt tcgctccgta cttcctggtg ttatccaggc tgttgaggca   1080

tccggacaca aggttatttg gcagtccgat ccgatgcacg gcaacacttt caccgcatcc   1140

aatggctaca agacccgtca cttcgacaag gttatcgatg aggtccaggg cttcttcgag   1200

gtccacgcgg cattgggcac ccacccaggc ggaatccaca ttgagttcac tggtgaagat   1260

gtcaccgagt gcctcggtgg cgctgaagac atcaccgatg ttgatctgcc aggccgctac   1320

gagtccgcat gcgatcctcg cctgaacact cagcagtctt tggagttggc tttcctcgtt   1380

gcagaaatgc tgcgtaacta a                                             1401
```

```
<210> SEQ ID NO 9
<211> LENGTH: 466
<212> TYPE: PRT
<213> ORGANISM: Artificial Sequence
<220> FEATURE:
<223> OTHER INFORMATION: aroG_E462A

<400> SEQUENCE: 9

Met Asn Arg Gly Val Ser Trp Thr Val Asp Ile Pro Lys Glu Val Leu
1               5                   10                  15

Pro Asp Leu Pro Pro Leu Pro Glu Gly Met Gln Gln Gln Phe Glu Asp
            20                  25                  30

Thr Ile Ser Arg Asp Ala Lys Gln Gln Pro Thr Trp Asp Arg Ala Gln
        35                  40                  45

Ala Glu Asn Val Arg Lys Ile Leu Glu Ser Val Pro Pro Ile Val Val
    50                  55                  60

Ala Pro Glu Val Leu Glu Leu Lys Gln Lys Leu Ala Asp Val Ala Asn
65                  70                  75                  80

Gly Lys Ala Phe Leu Leu Gln Gly Gly Asp Cys Ala Glu Thr Phe Glu
                85                  90                  95

Ser Asn Thr Glu Pro His Ile Arg Ala Asn Val Lys Thr Leu Leu Gln
            100                 105                 110

Met Ala Val Val Leu Thr Tyr Gly Ala Ser Thr Pro Val Ile Lys Met
        115                 120                 125

Ala Arg Ile Ala Gly Gln Tyr Ala Lys Pro Arg Ser Ser Asp Leu Asp
    130                 135                 140

Gly Asn Gly Leu Pro Asn Tyr Arg Gly Asp Ile Val Asn Gly Val Glu
```

-continued

```
145                 150                 155                 160

Ala Thr Pro Glu Ala Arg Arg His Asp Pro Ala Arg Met Ile Arg Ala
                165                 170                 175

Tyr Ala Asn Ala Ser Ala Ala Met Asn Leu Val Arg Ala Leu Thr Ser
            180                 185                 190

Ser Gly Thr Ala Asp Leu Tyr Arg Leu Ser Glu Trp Asn Arg Glu Phe
        195                 200                 205

Val Ala Asn Ser Pro Ala Gly Ala Arg Tyr Glu Ala Leu Ala Arg Glu
    210                 215                 220

Ile Asp Ser Gly Leu Arg Phe Met Glu Ala Cys Gly Val Ser Asp Glu
225                 230                 235                 240

Ser Leu Arg Ala Ala Asp Ile Tyr Cys Ser His Glu Ala Leu Leu Val
                245                 250                 255

Asp Tyr Glu Arg Ser Met Leu Arg Leu Ala Thr Asp Glu Glu Gly Asn
            260                 265                 270

Glu Glu Leu Tyr Asp Leu Ser Ala His Gln Leu Trp Ile Gly Glu Arg
        275                 280                 285

Thr Arg Gly Met Asp Asp Phe His Val Asn Phe Ala Ser Met Ile Ser
    290                 295                 300

Asn Pro Ile Gly Ile Lys Ile Gly Pro Gly Ile Thr Pro Glu Glu Ala
305                 310                 315                 320

Val Ala Tyr Ala Asp Lys Leu Asp Pro Asn Phe Glu Pro Gly Arg Leu
                325                 330                 335

Thr Ile Val Ala Arg Met Gly His Asp Lys Val Arg Ser Val Leu Pro
            340                 345                 350

Gly Val Ile Gln Ala Val Glu Ala Ser Gly His Lys Val Ile Trp Gln
        355                 360                 365

Ser Asp Pro Met His Gly Asn Thr Phe Thr Ala Ser Asn Gly Tyr Lys
    370                 375                 380

Thr Arg His Phe Asp Lys Val Ile Asp Glu Val Gln Gly Phe Phe Glu
385                 390                 395                 400

Val His Arg Ala Leu Gly Thr His Pro Gly Gly Ile His Ile Glu Phe
                405                 410                 415

Thr Gly Glu Asp Val Thr Glu Cys Leu Gly Gly Ala Glu Asp Ile Thr
            420                 425                 430

Asp Val Asp Leu Pro Gly Arg Tyr Glu Ser Ala Cys Asp Pro Arg Leu
        435                 440                 445

Asn Thr Gln Gln Ser Leu Glu Leu Ala Phe Leu Val Ala Ala Met Leu
    450                 455                 460

Arg Asn
465
```

<210> SEQ ID NO 10
<211> LENGTH: 1401
<212> TYPE: DNA
<213> ORGANISM: Artificial Sequence
<220> FEATURE:
<223> OTHER INFORMATION: aroG_E462A_nt

<400> SEQUENCE: 10

```
atgaataggg gtgtgagttg gacagttgat atccctaaag aagttctccc tgatttgcca     60

ccattgccag aaggcatgca gcagcagttc gaggacacca tttcccgtga cgctaagcag    120

caacctacgt gggatcgtgc acaggcagaa aacgtgcgca agatccttga gtcggttcct    180

ccaatcgttg ttgcccctga ggtacttgag ctgaagcaga agcttgctga tgttgccaac    240
```

ggtaaggcct tcctcttgca gggtggtgac tgtgcggaaa ctttcgagtc aaacactgag 300
ccgcacattc gcgccaacgt aaagactctg ctgcagatgg cagttgtttt gacctacggt 360
gcatccactc ctgtgatcaa gatggctcgt attgctggtc agtacgcaaa gcctcgctct 420
tctgatctgg atggaaatgg tctgccaaac taccgtggcg atatcgtcaa cggtgtggag 480
gcaaccccag aggctcgtcg ccacgatcct gcccgcatga tccgtgctta cgctaacgct 540
tctgctgcga tgaacttggt gcgcgcgctc accagctctg gcaccgctga tctttaccgt 600
ctcagcgagt ggaaccgcga gttcgttgcg aactccccag ctggtgcacg ctacgaggct 660
cttgctcgtg agatcgactc cggtctgcgc ttcatggaag catgtggcgt gtccgatgag 720
tccctgcgtg ctgcagatat ctactgctcc cacgaggctt tgctggtgga ttacgagcgt 780
tccatgctgc gtcttgcaac cgatgaggaa ggcaacgagg aactttacga tctttcagct 840
caccagctgt ggatcggcga gcgcacccgt ggcatggatg atttccatgt gaacttcgca 900
tccatgatct ctaacccaat cggcatcaag attggtcctg gtatcacccc tgaagaggct 960
gttgcatacg ctgacaagct cgatccgaac ttcgagcctg gccgtttgac catcgttgct 1020
cgcatgggcc acgacaaggt tcgctccgta cttcctggtg ttatccaggc tgttgaggca 1080
tccggacaca aggttatttg gcagtccgat ccgatgcacg gcaacacttt caccgcatcc 1140
aatggctaca agacccgtca cttcgacaag gttatcgatg aggtccaggg cttcttcgag 1200
gtccaccgcg cattgggcac ccacccaggc ggaatccaca ttgagttcac tggtgaagat 1260
gtcaccgagt gcctcggtgg cgctgaagac atcaccgatg ttgatctgcc aggccgctac 1320
gagtccgcat gcgatcctcg cctgaacact cagcagtctt tggagttggc tttcctcgtt 1380
gcagcgatgc tgcgtaacta a 1401

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tgatgcgcgt cataatttag 20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ctcatctctg actggacgtg 20

<210> SEQ ID NO 13
<211> LENGTH: 41
<212> TYPE: DNA
<213> ORGANISM: Artificial Sequence
<220> FEATURE:
<223> OTHER INFORMATION: primer

<400> SEQUENCE: 13
gtgaattcga gctcggtacc cagttgaatg ctaccaactt g 41

<210> SEQ ID NO 14

<211> LENGTH: 35
<212> TYPE: DNA
<213> ORGANISM: Artificial Sequence
<220> FEATURE:
<223> OTHER INFORMATION: primer

<400> SEQUENCE: 14
cacgagcaag agcctcgtac gctgcaccag ctggg 35

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
ggtcgactct agaggatccc cgctgttatt actgtgcctg 40

<210> SEQ ID NO 16
<211> LENGTH: 39
<212> TYPE: DNA
<213> ORGANISM: Artificial Sequence
<220> FEATURE:
<223> OTHER INFORMATION: primer

<400> SEQUENCE: 16
gaactcccca gctggtgcag cgtacgaggc tcttgctcg 39

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17
gggtgatacc aggaccaatc gcgatgccga ttgggttag 39

<210> SEQ ID NO 18
<211> LENGTH: 39
<212> TYPE: DNA
<213> ORGANISM: Artificial Sequence
<220> FEATURE:
<223> OTHER INFORMATION: primer

<400> SEQUENCE: 18
ctctaaccca atcggcatcg cgattggtcc tggtatcac 39

<210> SEQ ID NO 19
<211> LENGTH: 38
<212> TYPE: DNA
<213> ORGANISM: Artificial Sequence
<220> FEATURE:
<223> OTHER INFORMATION: primer

<400> SEQUENCE: 19
ctgggtgggt gcccaatgcc gcgtggacct cgaagaag 38

<210> SEQ ID NO 20
<211> LENGTH: 37
<212> TYPE: DNA
<213> ORGANISM: Artificial Sequence
<220> FEATURE:
<223> OTHER INFORMATION: primer

<400> SEQUENCE: 20
gggcttcttc gaggtccacg cggcattggg cacccac 37

<210> SEQ ID NO 21
<211> LENGTH: 38
<212> TYPE: DNA
<213> ORGANISM: Artificial Sequence
<220> FEATURE:
<223> OTHER INFORMATION: primer

<400> SEQUENCE: 21
aagcttagtt acgcagcatc gctgcaacga ggaaagcc 38

<210> SEQ ID NO 22
<211> LENGTH: 39
<212> TYPE: DNA
<213> ORGANISM: Artificial Sequence
<220> FEATURE:
<223> OTHER INFORMATION: primer

<400> SEQUENCE: 22
gttggctttc ctcgttgcag cgatgctgcg taactaagc 39

<210> SEQ ID NO 23
<211> LENGTH: 466
<212> TYPE: PRT
<213> ORGANISM: Artificial Sequence
<220> FEATURE:
<223> OTHER INFORMATION: aroG_R217A+K310A+E462A

<400> SEQUENCE: 23

Met Asn Arg Gly Val Ser Trp Thr Val Asp Ile Pro Lys Glu Val Leu
1 5 10 15

Pro Asp Leu Pro Pro Leu Pro Glu Gly Met Gln Gln Gln Phe Glu Asp
20 25 30

Thr Ile Ser Arg Asp Ala Lys Gln Gln Pro Thr Trp Asp Arg Ala Gln
35 40 45

Ala Glu Asn Val Arg Lys Ile Leu Glu Ser Val Pro Pro Ile Val Val
50 55 60

Ala Pro Glu Val Leu Glu Leu Lys Gln Lys Leu Ala Asp Val Ala Asn
65 70 75 80

Gly Lys Ala Phe Leu Leu Gln Gly Gly Asp Cys Ala Glu Thr Phe Glu
85 90 95

Ser Asn Thr Glu Pro His Ile Arg Ala Asn Val Lys Thr Leu Leu Gln
100 105 110

Met Ala Val Val Leu Thr Tyr Gly Ala Ser Thr Pro Val Ile Lys Met
115 120 125

Ala Arg Ile Ala Gly Gln Tyr Ala Lys Pro Arg Ser Ser Asp Leu Asp
130 135 140

Gly Asn Gly Leu Pro Asn Tyr Arg Gly Asp Ile Val Asn Gly Val Glu
145 150 155 160

Ala Thr Pro Glu Ala Arg Arg His Asp Pro Ala Arg Met Ile Arg Ala
165 170 175

Tyr Ala Asn Ala Ser Ala Ala Met Asn Leu Val Arg Ala Leu Thr Ser
180 185 190

Ser Gly Thr Ala Asp Leu Tyr Arg Leu Ser Glu Trp Asn Arg Glu Phe
195 200 205

Val Ala Asn Ser Pro Ala Gly Ala Ala Tyr Glu Ala Leu Ala Arg Glu
210 215 220

```
Ile Asp Ser Gly Leu Arg Phe Met Glu Ala Cys Gly Val Ser Asp Glu
225                 230                 235                 240

Ser Leu Arg Ala Ala Asp Ile Tyr Cys Ser His Glu Ala Leu Leu Val
                245                 250                 255

Asp Tyr Glu Arg Ser Met Leu Arg Leu Ala Thr Asp Glu Glu Gly Asn
            260                 265                 270

Glu Glu Leu Tyr Asp Leu Ser Ala His Gln Leu Trp Ile Gly Glu Arg
        275                 280                 285

Thr Arg Gly Met Asp Asp Phe His Val Asn Phe Ala Ser Met Ile Ser
    290                 295                 300

Asn Pro Ile Gly Ile Ala Ile Gly Pro Gly Ile Thr Pro Glu Glu Ala
305                 310                 315                 320

Val Ala Tyr Ala Asp Lys Leu Asp Pro Asn Phe Glu Pro Gly Arg Leu
                325                 330                 335

Thr Ile Val Ala Arg Met Gly His Asp Lys Val Arg Ser Val Leu Pro
            340                 345                 350

Gly Val Ile Gln Ala Val Glu Ala Ser Gly His Lys Val Ile Trp Gln
        355                 360                 365

Ser Asp Pro Met His Gly Asn Thr Phe Thr Ala Ser Asn Gly Tyr Lys
    370                 375                 380

Thr Arg His Phe Asp Lys Val Ile Asp Glu Val Gln Gly Phe Phe Glu
385                 390                 395                 400

Val His Arg Ala Leu Gly Thr His Pro Gly Gly Ile His Ile Glu Phe
                405                 410                 415

Thr Gly Glu Asp Val Thr Glu Cys Leu Gly Gly Ala Glu Asp Ile Thr
            420                 425                 430

Asp Val Asp Leu Pro Gly Arg Tyr Glu Ser Ala Cys Asp Pro Arg Leu
        435                 440                 445

Asn Thr Gln Gln Ser Leu Glu Leu Ala Phe Leu Val Ala Ala Met Leu
    450                 455                 460

Arg Asn
465
```

<210> SEQ ID NO 24
<211> LENGTH: 1401
<212> TYPE: DNA
<213> ORGANISM: Artificial Sequence
<220> FEATURE:
<223> OTHER INFORMATION: aroG_R217A+K310A+E462A_nt

<400> SEQUENCE: 24

```
atgaataggg gtgtgagttg gacagttgat atccctaaag aagttctccc tgatttgcca      60

ccattgccag aaggcatgca gcagcagttc gaggacacca tttcccgtga cgctaagcag     120

caacctacgt gggatcgtgc acaggcagaa aacgtgcgca agatccttga gtcggttcct     180

ccaatcgttg ttgcccctga ggtacttgag ctgaagcaga agcttgctga tgttgccaac     240

ggtaaggcct tcctcttgca gggtggtgac tgtgcggaaa ctttcgagtc aaacactgag     300

ccgcacattc gcgccaacgt aaagactctg ctgcagatgg cagttgtttt gacctacggt     360

gcatccactc ctgtgatcaa gatggctcgt attgctggtc agtacgcaaa gcctcgctct     420

tctgatctgg atggaaatgg tctgccaaac taccgtggcg atatcgtcaa cggtgtggag     480

gcaaccccag aggctcgtcg ccacgatcct gcccgcatga tccgtgctta cgctaacgct     540

tctgctgcga tgaacttggt gcgcgcgctc accagctctg gcaccgctga tctttaccgt     600

ctcagcgagt ggaaccgcga gttcgttgcg aactccccag ctggtgcagc gtacgaggct     660
```

```
cttgctcgtg agatcgactc cggtctgcgc ttcatggaag catgtggcgt gtccgatgag    720

tccctgcgtg ctgcagatat ctactgctcc cacgaggctt tgctggtgga ttacgagcgt    780

tccatgctgc gtcttgcaac cgatgaggaa ggcaacgagg aactttacga tctttcagct    840

caccagctgt ggatcggcga gcgcacccgt ggcatggatg atttccatgt gaacttcgca    900

tccatgatct ctaacccaat cggcatcgcg attggtcctg gtatcacccc tgaagaggct    960

gttgcatacg ctgacaagct cgatccgaac ttcgagcctg gccgtttgac catcgttgct   1020

cgcatgggcc acgacaaggt tcgctccgta cttcctggtg ttatccaggc tgttgaggca   1080

tccggacaca aggttatttg gcagtccgat ccgatgcacg gcaacacttt caccgcatcc   1140

aatggctaca agacccgtca cttcgacaag gttatcgatg aggtccaggg cttcttcgag   1200

gtccaccgcg cattgggcac ccacccaggc ggaatccaca ttgagttcac tggtgaagat   1260

gtcaccgagt gcctcggtgg cgctgaagac atcaccgatg ttgatctgcc aggccgctac   1320

gagtccgcat gcgatcctcg cctgaacact cagcagtctt tggagttggc tttcctcgtt   1380

gcagcgatgc tgcgtaacta a                                              1401
```

<210> SEQ ID NO 25
<211> LENGTH: 466
<212> TYPE: PRT
<213> ORGANISM: Artificial Sequence
<220> FEATURE:
<223> OTHER INFORMATION: aroG_R217A+K310A+R403A+E462A

<400> SEQUENCE: 25

```
Met Asn Arg Gly Val Ser Trp Thr Val Asp Ile Pro Lys Glu Val Leu
1               5                   10                  15

Pro Asp Leu Pro Pro Leu Pro Glu Gly Met Gln Gln Gln Phe Glu Asp
            20                  25                  30

Thr Ile Ser Arg Asp Ala Lys Gln Gln Pro Thr Trp Asp Arg Ala Gln
        35                  40                  45

Ala Glu Asn Val Arg Lys Ile Leu Glu Ser Val Pro Pro Ile Val Val
    50                  55                  60

Ala Pro Glu Val Leu Glu Leu Lys Gln Lys Leu Ala Asp Val Ala Asn
65                  70                  75                  80

Gly Lys Ala Phe Leu Leu Gln Gly Gly Asp Cys Ala Glu Thr Phe Glu
                85                  90                  95

Ser Asn Thr Glu Pro His Ile Arg Ala Asn Val Lys Thr Leu Leu Gln
            100                 105                 110

Met Ala Val Val Leu Thr Tyr Gly Ala Ser Thr Pro Val Ile Lys Met
        115                 120                 125

Ala Arg Ile Ala Gly Gln Tyr Ala Lys Pro Arg Ser Ser Asp Leu Asp
    130                 135                 140

Gly Asn Gly Leu Pro Asn Tyr Arg Gly Asp Ile Val Asn Gly Val Glu
145                 150                 155                 160

Ala Thr Pro Glu Ala Arg Arg His Asp Pro Ala Arg Met Ile Arg Ala
                165                 170                 175

Tyr Ala Asn Ala Ser Ala Ala Met Asn Leu Val Arg Ala Leu Thr Ser
            180                 185                 190

Ser Gly Thr Ala Asp Leu Tyr Arg Leu Ser Glu Trp Asn Arg Glu Phe
        195                 200                 205

Val Ala Asn Ser Pro Ala Gly Ala Ala Tyr Glu Ala Leu Ala Arg Glu
    210                 215                 220
```

```
Ile Asp Ser Gly Leu Arg Phe Met Glu Ala Cys Gly Val Ser Asp Glu
225                 230                 235                 240

Ser Leu Arg Ala Ala Asp Ile Tyr Cys Ser His Glu Ala Leu Leu Val
                245                 250                 255

Asp Tyr Glu Arg Ser Met Leu Arg Leu Ala Thr Asp Glu Glu Gly Asn
            260                 265                 270

Glu Glu Leu Tyr Asp Leu Ser Ala His Gln Leu Trp Ile Gly Glu Arg
        275                 280                 285

Thr Arg Gly Met Asp Asp Phe His Val Asn Phe Ala Ser Met Ile Ser
    290                 295                 300

Asn Pro Ile Gly Ile Ala Ile Gly Pro Gly Ile Thr Pro Glu Glu Ala
305                 310                 315                 320

Val Ala Tyr Ala Asp Lys Leu Asp Pro Asn Phe Glu Pro Gly Arg Leu
                325                 330                 335

Thr Ile Val Ala Arg Met Gly His Asp Lys Val Arg Ser Val Leu Pro
            340                 345                 350

Gly Val Ile Gln Ala Val Glu Ala Ser Gly His Lys Val Ile Trp Gln
        355                 360                 365

Ser Asp Pro Met His Gly Asn Thr Phe Thr Ala Ser Asn Gly Tyr Lys
    370                 375                 380

Thr Arg His Phe Asp Lys Val Ile Asp Glu Val Gln Gly Phe Phe Glu
385                 390                 395                 400

Val His Ala Ala Leu Gly Thr His Pro Gly Gly Ile His Ile Glu Phe
                405                 410                 415

Thr Gly Glu Asp Val Thr Glu Cys Leu Gly Gly Ala Glu Asp Ile Thr
            420                 425                 430

Asp Val Asp Leu Pro Gly Arg Tyr Glu Ser Ala Cys Asp Pro Arg Leu
        435                 440                 445

Asn Thr Gln Gln Ser Leu Glu Leu Ala Phe Leu Val Ala Ala Met Leu
    450                 455                 460

Arg Asn
465
```

<210> SEQ ID NO 26
<211> LENGTH: 1401
<212> TYPE: DNA
<213> ORGANISM: Artificial Sequence
<220> FEATURE:
<223> OTHER INFORMATION: aroG_R217A+K310A+R403A+E462A_nt

<400> SEQUENCE: 26

```
atgaataggg gtgtgagttg gacagttgat atccctaaag aagttctccc tgatttgcca     60

ccattgccag aaggcatgca gcagcagttc gaggacacca tttcccgtga cgctaagcag    120

caacctacgt gggatcgtgc acaggcagaa aacgtgcgca agatccttga gtcggttcct    180

ccaatcgttg ttgcccctga ggtacttgag ctgaagcaga agcttgctga tgttgccaac    240

ggtaaggcct tcctcttgca gggtggtgac tgtgcggaaa ctttcgagtc aaacactgag    300

ccgcacattc gcgccaacgt aaagactctg ctgcagatgg cagttgtttt gacctacggt    360

gcatccactc ctgtgatcaa gatggctcgt attgctggtc agtacgcaaa gcctcgctct    420

tctgatctgg atggaaatgg tctgccaaac taccgtggcg atatcgtcaa cggtgtggag    480

gcaaccccag aggctcgtcg ccacgatcct gcccgcatga tccgtgctta cgctaacgct    540

tctgctgcga tgaacttggt gcgcgcgctc accagctctg gcaccgctga tctttaccgt    600

ctcagcgagt ggaaccgcga gttcgttgcg aactccccag ctggtgcagc gtacgaggct    660
```

cttgctcgtg agatcgactc cggtctgcgc ttcatggaag catgtggcgt gtccgatgag 720
tccctgcgtg ctgcagatat ctactgctcc cacgaggctt tgctggtgga ttacgagcgt 780
tccatgctgc gtcttgcaac cgatgaggaa ggcaacgagg aactttacga tctttcagct 840
caccagctgt ggatcggcga gcgcacccgt ggcatggatg atttccatgt gaacttcgca 900
tccatgatct ctaacccaat cggcatcgcg attggtcctg gtatcacccc tgaagaggct 960
gttgcatacg ctgacaagct cgatccgaac ttcgagcctg gccgtttgac catcgttgct 1020
cgcatgggcc acgacaaggt tcgctccgta cttcctggtg ttatccaggc tgttgaggca 1080
tccggacaca aggttatttg gcagtccgat ccgatgcacg gcaacacttt caccgcatcc 1140
aatggctaca agacccgtca cttcgacaag gttatcgatg aggtccaggg cttcttcgag 1200
gtccacgcgg cattgggcac ccacccaggc ggaatccaca ttgagttcac tggtgaagat 1260
gtcaccgagt gcctcggtgg cgctgaagac atcaccgatg ttgatctgcc aggccgctac 1320
gagtccgcat gcgatcctcg cctgaacact cagcagtctt tggagttggc tttcctcgtt 1380
gcagcgatgc tgcgtaacta a 1401

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
tatgcttcac cacatgactt c 21

<210> SEQ ID NO 28
<211> LENGTH: 23
<212> TYPE: DNA
<213> ORGANISM: Artificial Sequence
<220> FEATURE:
<223> OTHER INFORMATION: primer

<400> SEQUENCE: 28
aaatcatttg agaaaactcg agg 23

<210> SEQ ID NO 29
<211> LENGTH: 19
<212> TYPE: DNA
<213> ORGANISM: Artificial Sequence
<220> FEATURE:
<223> OTHER INFORMATION: primer

<400> SEQUENCE: 29
gtcacccgat cgtctgaag 19

<210> SEQ ID NO 30
<211> LENGTH: 18
<212> TYPE: DNA
<213> ORGANISM: Artificial Sequence
<220> FEATURE:
<223> OTHER INFORMATION: primer

<400> SEQUENCE: 30
gtcttaaaac cggttgat 18

<210> SEQ ID NO 31
<211> LENGTH: 19
<212> TYPE: DNA

<213> ORGANISM: Artificial Sequence
<220> FEATURE:
<223> OTHER INFORMATION: primer

<400> SEQUENCE: 31
caatgctggc tgcgtacgc 19

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
ctcctcgcga ggaaccaact 20

<210> SEQ ID NO 33
<211> LENGTH: 35
<212> TYPE: DNA
<213> ORGANISM: Artificial Sequence
<220> FEATURE:
<223> OTHER INFORMATION: primer

<400> SEQUENCE: 33
tcgagctcgg taccccgctt ttgcactcat cgagc 35

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
cacgatcaga tgtgcatcat cat 23

<210> SEQ ID NO 35
<211> LENGTH: 23
<212> TYPE: DNA
<213> ORGANISM: Artificial Sequence
<220> FEATURE:
<223> OTHER INFORMATION: primer

<400> SEQUENCE: 35
atgatgatgc acatctgatc gtg 23

<210> SEQ ID NO 36
<211> LENGTH: 35
<212> TYPE: DNA
<213> ORGANISM: Artificial Sequence
<220> FEATURE:
<223> OTHER INFORMATION: primer

<400> SEQUENCE: 36
ctctagagga tccccgagca tcttccaaaa ccttg 35

<210> SEQ ID NO 37
<211> LENGTH: 35
<212> TYPE: DNA
<213> ORGANISM: Artificial Sequence
<220> FEATURE:
<223> OTHER INFORMATION: primer

<400> SEQUENCE: 37
tcgagctcgg tacccatgag tgaaacatac gtgtc 35

<210> SEQ ID NO 38
<211> LENGTH: 39
<212> TYPE: DNA
<213> ORGANISM: Artificial Sequence
<220> FEATURE:
<223> OTHER INFORMATION: primer

<400> SEQUENCE: 38
gcgcttgagg tactctgcca gcgcgatgtc atcatccgg 39

<210> SEQ ID NO 39
<211> LENGTH: 39
<212> TYPE: DNA
<213> ORGANISM: Artificial Sequence
<220> FEATURE:
<223> OTHER INFORMATION: primer

<400> SEQUENCE: 39
ccggatgatg acatcgcgct ggcagagtac ctcaagcgc 39

<210> SEQ ID NO 40
<211> LENGTH: 34
<212> TYPE: DNA
<213> ORGANISM: Artificial Sequence
<220> FEATURE:
<223> OTHER INFORMATION: primer

<400> SEQUENCE: 40
ctctagagga tcccccgtca ccgacacctc caca 34

<210> SEQ ID NO 41
<211> LENGTH: 437
<212> TYPE: PRT
<213> ORGANISM: Artificial Sequence
<220> FEATURE:
<223> OTHER INFORMATION: gltA_M312I

<400> SEQUENCE: 41

```
Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175
```

```
Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
    290                 295                 300

Lys Glu Asp Gly Val Arg Leu Ile Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
        355                 360                 365

Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Asn Glu Ser Arg Lys Leu Val
            420                 425                 430

Pro Arg Glu Glu Arg
        435


<210> SEQ ID NO 42
<211> LENGTH: 1314
<212> TYPE: DNA
<213> ORGANISM: Artificial Sequence
<220> FEATURE:
<223> OTHER INFORMATION: gltA_M312I_nt

<400> SEQUENCE: 42

atgtttgaaa gggatatcgt ggctactgat aacaacaagg ctgtcctgca ctaccccggt      60

ggcgagttcg aaatggacat catcgaggct tctgagggta acaacggtgt tgtcctgggc     120

aagatgctgt ctgagactgg actgatcact tttgacccag gttatgtgag cactggctcc     180

accgagtcga agatcaccta catcgatggc gatgcgggaa tcctgcgtta ccgcggctat     240

gacatcgctg atctggctga gaatgccacc ttcaacgagg tttcttacct acttatcaac     300

ggtgagctac caaccccaga tgagcttcac aagtttaacg acgagattcg ccaccacacc     360

cttctggacg aggacttcaa gtcccagttc aacgtgttcc cacgcgacgc tcacccaatg     420

gcaaccttgg cttcctcggt taacattttg tctacctact accaggacca gctgaaccca     480

ctcgatgagg cacagcttga taaggcaacc gttcgcctca tggcaaaggt tccaatgctg     540
```

gctgcgtacg cacaccgcgc acgcaagggt gctccttaca tgtacccaga caactccctc 600
aatgcgcgtg agaacttcct gcgcatgatg ttcggttacc caaccgagcc atacgagatc 660
gacccaatca tggtcaaggc tctggacaag ctgctcatcc tgcacgctga ccacgagcag 720
aactgctcca cctccaccgt tcgtatgatc ggttccgcac aggccaacat gtttgtctcc 780
atcgctggtg gcatcaacgc tctgtccggc ccactgcacg gtggcgcaaa ccaggctgtt 840
ctggagatgc tcgaagacat caagagcaac cacggtggcg acgcaaccga gttcatgaac 900
aaggtcaaga acaaggaaga cggcgtccgc ctcatcggct tcggacaccg cgtttacaag 960
aactacgatc cacgtgcagc aatcgtcaag gagaccgcac acgagatcct cgagcacctc 1020
ggtggcgacg atcttctgga tctggcaatc aagctggaag aaattgcact ggctgatgat 1080
tacttcatct cccgcaagct ctacccgaac gtagacttct acaccggcct gatctaccgc 1140
gcaatgggct tcccaactga cttcttcacc gtattgttcg caatcggtcg tctgccagga 1200
tggatcgctc actaccgcga gcagctcggt gcagcaggca acaagatcaa ccgcccacgc 1260
caggtctaca ccggcaacga atcccgcaag ttggttcctc gcgaggagcg ctaa 1314

<210> SEQ ID NO 43
<211> LENGTH: 42
<212> TYPE: DNA
<213> ORGANISM: Artificial Sequence
<220> FEATURE:
<223> OTHER INFORMATION: gltA M312I Up F

<400> SEQUENCE: 43
gtgaattcga gctcggtacc cgcgggaatc ctgcgttacc gc 42

<210> SEQ ID NO 44
<211> LENGTH: 42
<212> TYPE: DNA
<213> ORGANISM: Artificial Sequence
<220> FEATURE:
<223> OTHER INFORMATION: gltA M312I Up R

<400> SEQUENCE: 44
tgtaaacgcg gtgtccgaag ccgatgaggc ggacgccgtc tt 42

<210> SEQ ID NO 45
<211> LENGTH: 42
<212> TYPE: DNA
<213> ORGANISM: Artificial Sequence
<220> FEATURE:
<223> OTHER INFORMATION: gltA M312I Down F

<400> SEQUENCE: 45
aagacggcgt ccgcctcatc ggcttcggac accgcgttta ca 42

<210> SEQ ID NO 46
<211> LENGTH: 42
<212> TYPE: DNA
<213> ORGANISM: Artificial Sequence
<220> FEATURE:
<223> OTHER INFORMATION: gltA M312I Down R

<400> SEQUENCE: 46
ggtcgactct agaggatccc cttagcgctc ctcgcgagga ac 42

<210> SEQ ID NO 47
<211> LENGTH: 436
<212> TYPE: PRT

<213> ORGANISM: Unknown
<220> FEATURE:
<223> OTHER INFORMATION: ilvA_WT

<400> SEQUENCE: 47

```
Met Ser Glu Thr Tyr Val Ser Glu Lys Ser Pro Gly Val Met Ala Ser
1               5                   10                  15

Gly Ala Glu Leu Ile Arg Ala Ala Asp Ile Gln Thr Ala Gln Ala Arg
            20                  25                  30

Ile Ser Ser Val Ile Ala Pro Thr Pro Leu Gln Tyr Cys Pro Arg Leu
        35                  40                  45

Ser Glu Glu Thr Gly Ala Glu Ile Tyr Leu Lys Arg Glu Asp Leu Gln
    50                  55                  60

Asp Val Arg Ser Tyr Lys Ile Arg Gly Ala Leu Asn Ser Gly Ala Gln
65                  70                  75                  80

Leu Thr Gln Glu Gln Arg Asp Ala Gly Ile Val Ala Ala Ser Ala Gly
                85                  90                  95

Asn His Ala Gln Gly Val Ala Tyr Val Cys Lys Ser Leu Gly Val Gln
            100                 105                 110

Gly Arg Ile Tyr Val Pro Val Gln Thr Pro Lys Gln Lys Arg Asp Arg
        115                 120                 125

Ile Met Val His Gly Gly Glu Phe Val Ser Leu Val Val Thr Gly Asn
    130                 135                 140

Asn Phe Asp Glu Ala Ser Ala Ala Ala His Glu Asp Ala Glu Arg Thr
145                 150                 155                 160

Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
            180                 185                 190

Lys Ser Ala Asp His Val Met Val Pro Val Gly Gly Gly Gly Leu Leu
        195                 200                 205

Ala Gly Val Val Ser Tyr Met Ala Asp Met Ala Pro Arg Thr Ala Ile
    210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Ala Val Lys Arg Val Gly Asp Leu Asn Tyr Thr Ile Val Glu Lys
            260                 265                 270

Asn Gln Gly Arg Val His Met Met Ser Ala Thr Glu Gly Ala Val Cys
        275                 280                 285

Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320

Gly Ser Val Val Val Cys Ile Ile Ser Gly Gly Asn Asn Asp Val Leu
                325                 330                 335

Arg Tyr Ala Glu Ile Ala Glu Arg Ser Leu Val His Arg Gly Leu Lys
            340                 345                 350

His Tyr Phe Leu Val Asn Phe Pro Gln Lys Pro Gly Gln Leu Arg His
        355                 360                 365

Phe Leu Glu Asp Ile Leu Gly Pro Asp Asp Asp Ile Thr Leu Phe Glu
    370                 375                 380

Tyr Leu Lys Arg Asn Asn Arg Glu Thr Gly Thr Ala Leu Val Gly Ile
```

385 390 395 400

His Leu Ser Glu Ala Ser Gly Leu Asp Ser Leu Leu Glu Arg Met Glu
405 410 415

Glu Ser Ala Ile Asp Ser Arg Arg Leu Glu Pro Gly Thr Pro Glu Tyr
420 425 430

Glu Tyr Leu Thr
435

<210> SEQ ID NO 48
<211> LENGTH: 1311
<212> TYPE: DNA
<213> ORGANISM: Unknown
<220> FEATURE:
<223> OTHER INFORMATION: ilvA_WT_nt

<400> SEQUENCE: 48
atgagtgaaa catacgtgtc tgagaaaagt ccaggagtga tggctagcgg agcggagctg 60
attcgtgccg ccgacattca aacggcgcag gcacgaattt cctccgtcat tgcaccaact 120
ccattgcagt attgccctcg tctttctgag gaaaccggag cggaaatcta ccttaagcgt 180
gaggatctgc aggatgttcg ttcctacaag atccgcggtg cgctgaactc tggagcgcag 240
ctcacccaag agcagcgcga tgcaggtatc gttgccgcat ctgcaggtaa ccatgcccag 300
ggcgtggcct atgtgtgcaa gtccttgggc gttcagggac gcatctatgt tcctgtgcag 360
actccaaagc aaaagcgtga ccgcatcatg gttcacggcg gagagtttgt ctccttggtg 420
gtcactggca ataacttcga cgaagcatcg gctgcagcgc atgaagatgc agagcgcacc 480
ggcgcaacgc tgatcgagcc tttcgatgct cgcaacaccg tcatcggtca gggcaccgtg 540
gctgctgaga tcttgtcgca gctgacttcc atgggcaaga gtgcagatca cgtgatggtt 600
ccagtcggcg gtggcggact tcttgcaggt gtggtcagct acatggctga tatggcacct 660
cgcactgcga tcgttggtat cgaaccagcg ggagcagcat ccatgcaggc tgcattgcac 720
aatggtggac caatcacttt ggagactgtt gatccctttg tggacggcgc agcagtcaaa 780
cgtgtcggag atctcaacta caccatcgtg gagaagaacc agggtcgcgt gcacatgatg 840
agcgcgaccg agggcgctgt gtgtactgag atgctcgatc tttaccaaaa cgaaggcatc 900
atcgcggagc ctgctggcgc gctgtctatc gctgggttga aggaaatgtc ctttgcacct 960
ggttctgtcg tggtgtgcat catctctggt ggcaacaacg atgtgctgcg ttatgcggaa 1020
atcgctgagc gctccttggt gcaccgcggt ttgaagcact acttcttggt gaacttcccg 1080
caaaagcctg gtcagttgcg tcacttcctg gaagatatcc tgggaccgga tgatgacatc 1140
acgctgtttg agtacctcaa gcgcaacaac cgtgagaccg gtactgcgtt ggtgggtatt 1200
cacttgagtg aagcatcagg attggattct ttgctggaac gtatggagga atcggcaatt 1260
gattcccgtc gcctcgagcc gggcacccct gagtacgaat acttgaccta a 1311

<210> SEQ ID NO 49
<211> LENGTH: 26
<212> TYPE: DNA
<213> ORGANISM: Artificial Sequence
<220> FEATURE:
<223> OTHER INFORMATION: primer

<400> SEQUENCE: 49
ggatccgact gagcctgggc aactgg 26

<210> SEQ ID NO 50

<211> LENGTH: 26
<212> TYPE: DNA
<213> ORGANISM: Artificial Sequence
<220> FEATURE:
<223> OTHER INFORMATION: primer

<400> SEQUENCE: 50
ggatccccgt caccgacacc tccaca 26

<210> SEQ ID NO 51
<211> LENGTH: 25
<212> TYPE: DNA
<213> ORGANISM: Artificial Sequence
<220> FEATURE:
<223> OTHER INFORMATION: primer

<400> SEQUENCE: 51
acatcacgct ggcagagtac ctcaa 25

<210> SEQ ID NO 52
<211> LENGTH: 25
<212> TYPE: DNA
<213> ORGANISM: Artificial Sequence
<220> FEATURE:
<223> OTHER INFORMATION: primer

<400> SEQUENCE: 52
ttgaggtact ctgccagcgt gatgt 25

<210> SEQ ID NO 53
<211> LENGTH: 436
<212> TYPE: PRT
<213> ORGANISM: Artificial Sequence
<220> FEATURE:
<223> OTHER INFORMATION: ilvA_T381A+F383A

<400> SEQUENCE: 53

Met Ser Glu Thr Tyr Val Ser Glu Lys Ser Pro Gly Val Met Ala Ser
1 5 10 15

Gly Ala Glu Leu Ile Arg Ala Ala Asp Ile Gln Thr Ala Gln Ala Arg
20 25 30

Ile Ser Ser Val Ile Ala Pro Thr Pro Leu Gln Tyr Cys Pro Arg Leu
35 40 45

Ser Glu Glu Thr Gly Ala Glu Ile Tyr Leu Lys Arg Glu Asp Leu Gln
50 55 60

Asp Val Arg Ser Tyr Lys Ile Arg Gly Ala Leu Asn Ser Gly Ala Gln
65 70 75 80

Leu Thr Gln Glu Gln Arg Asp Ala Gly Ile Val Ala Ala Ser Ala Gly
85 90 95

Asn His Ala Gln Gly Val Ala Tyr Val Cys Lys Ser Leu Gly Val Gln
100 105 110

Gly Arg Ile Tyr Val Pro Val Gln Thr Pro Lys Gln Lys Arg Asp Arg
115 120 125

Ile Met Val His Gly Gly Glu Phe Val Ser Leu Val Val Thr Gly Asn
130 135 140

Asn Phe Asp Glu Ala Ser Ala Ala Ala His Glu Asp Ala Glu Arg Thr
145 150 155 160

Gly Ala Thr Leu Ile Glu Pro Phe Asp Ala Arg Asn Thr Val Ile Gly
165 170 175

Gln Gly Thr Val Ala Ala Glu Ile Leu Ser Gln Leu Thr Ser Met Gly
180 185 190

```
Lys Ser Ala Asp His Val Met Val Pro Val Gly Gly Gly Gly Leu Leu
        195                 200                 205

Ala Gly Val Val Ser Tyr Met Ala Asp Met Ala Pro Arg Thr Ala Ile
    210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Ala Val Lys Arg Val Gly Asp Leu Asn Tyr Thr Ile Val Glu Lys
            260                 265                 270

Asn Gln Gly Arg Val His Met Met Ser Ala Thr Glu Gly Ala Val Cys
        275                 280                 285

Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320

Gly Ser Val Val Val Cys Ile Ile Ser Gly Gly Asn Asn Asp Val Leu
                325                 330                 335

Arg Tyr Ala Glu Ile Ala Glu Arg Ser Leu Val His Arg Gly Leu Lys
            340                 345                 350

His Tyr Phe Leu Val Asn Phe Pro Gln Lys Pro Gly Gln Leu Arg His
        355                 360                 365

Phe Leu Glu Asp Ile Leu Gly Pro Asp Asp Asp Ile Ala Leu Ala Glu
    370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
                405                 410                 415

Glu Ser Ala Ile Asp Ser Arg Arg Leu Glu Pro Gly Thr Pro Glu Tyr
            420                 425                 430

Glu Tyr Leu Thr
        435
```

<210> SEQ ID NO 54
<211> LENGTH: 1311
<212> TYPE: DNA
<213> ORGANISM: Artificial Sequence
<220> FEATURE:
<223> OTHER INFORMATION: ilvA_T381A+F383A_nt

<400> SEQUENCE: 54

```
atgagtgaaa catacgtgtc tgagaaaagt ccaggagtga tggctagcgg agcggagctg      60

attcgtgccg ccgacattca aacggcgcag gcacgaattt cctccgtcat tgcaccaact     120

ccattgcagt attgccctcg tctttctgag gaaaccggag cggaaatcta ccttaagcgt     180

gaggatctgc aggatgttcg ttcctacaag atccgcggtg cgctgaactc tggagcgcag     240

ctcacccaag agcagcgcga tgcaggtatc gttgccgcat ctgcaggtaa ccatgcccag     300

ggcgtggcct atgtgtgcaa gtccttgggc gttcagggac gcatctatgt tcctgtgcag     360

actccaaagc aaaagcgtga ccgcatcatg gttcacggcg gagagtttgt ctccttggtg     420

gtcactggca ataacttcga cgaagcatcg gctgcagcgc atgaagatgc agagcgcacc     480

ggcgcaacgc tgatcgagcc tttcgatgct cgcaacaccg tcatcggtca gggcaccgtg     540

gctgctgaga tcttgtcgca gctgacttcc atgggcaaga gtgcagatca cgtgatggtt     600
```

ccagtcggcg gtggcggact tcttgcaggt gtggtcagct acatggctga tatggcacct 660
cgcactgcga tcgttggtat cgaaccagcg ggagcagcat ccatgcaggc tgcattgcac 720
aatggtggac caatcacttt ggagactgtt gatccctttg tggacggcgc agcagtcaaa 780
cgtgtcggag atctcaacta caccatcgtg gagaagaacc agggtcgcgt gcacatgatg 840
agcgcgaccg agggcgctgt gtgtactgag atgctcgatc tttaccaaaa cgaaggcatc 900
atcgcggagc ctgctggcgc gctgtctatc gctgggttga aggaaatgtc ctttgcacct 960
ggttctgtcg tggtgtgcat catctctggt ggcaacaacg atgtgctgcg ttatgcggaa 1020
atcgctgagc gctccttggt gcaccgcggt ttgaagcact acttcttggt gaacttcccg 1080
caaaagcctg gtcagttgcg tcacttcctg gaagatatcc tgggaccgga tgatgacatc 1140
gcgctggcag agtacctcaa gcgcaacaac cgtgagaccg gtactgcgtt ggtgggtatt 1200
cacttgagtg aagcatcagg attggattct ttgctggaac gtatggagga atcggcaatt 1260
gattcccgtc gcctcgagcc gggcacccct gagtacgaat acttgaccta a 1311

<210> SEQ ID NO 55
<211> LENGTH: 22
<212> TYPE: DNA
<213> ORGANISM: Artificial Sequence
<220> FEATURE:
<223> OTHER INFORMATION: primer

<400> SEQUENCE: 55
aacacgaccg gcatcccgtc gc 22

<210> SEQ ID NO 56
<211> LENGTH: 23
<212> TYPE: DNA
<213> ORGANISM: Artificial Sequence
<220> FEATURE:
<223> OTHER INFORMATION: primer

<400> SEQUENCE: 56
aaatcatttg agaaaactcg agg 23

<210> SEQ ID NO 57
<211> LENGTH: 45
<212> TYPE: DNA
<213> ORGANISM: Artificial Sequence
<220> FEATURE:
<223> OTHER INFORMATION: primer

<400> SEQUENCE: 57
gtgaattcga gctcggtacc caaatcattt gagaaaactc gaggc 45

<210> SEQ ID NO 58
<211> LENGTH: 45
<212> TYPE: DNA
<213> ORGANISM: Artificial Sequence
<220> FEATURE:
<223> OTHER INFORMATION: primer

<400> SEQUENCE: 58
ggtgatcatc tcaacggtgg aacacaggtt gatgatcatt gggtt 45

<210> SEQ ID NO 59
<211> LENGTH: 45
<212> TYPE: DNA
<213> ORGANISM: Artificial Sequence
<220> FEATURE:
<223> OTHER INFORMATION: primer

<400> SEQUENCE: 59
aacccaatga tcatcaacct gtgttccacc gttgagatga tcacc 45

<210> SEQ ID NO 60
<211> LENGTH: 42
<212> TYPE: DNA
<213> ORGANISM: Artificial Sequence
<220> FEATURE:
<223> OTHER INFORMATION: primer

<400> SEQUENCE: 60
ggtcgactct agaggatccc caagaaggca acatcggaca gc 42

<210> SEQ ID NO 61
<211> LENGTH: 21
<212> TYPE: DNA
<213> ORGANISM: Artificial Sequence
<220> FEATURE:
<223> OTHER INFORMATION: primer

<400> SEQUENCE: 61
atccattcaa tggagtctgc g 21

<210> SEQ ID NO 62
<211> LENGTH: 616
<212> TYPE: PRT
<213> ORGANISM: Artificial Sequence
<220> FEATURE:
<223> OTHER INFORMATION: leuA_P247C+R558H+G561D

<400> SEQUENCE: 62

Met Ser Pro Asn Asp Ala Phe Ile Ser Ala Pro Ala Lys Ile Glu Thr
1 5 10 15

Pro Val Gly Pro Arg Asn Glu Gly Gln Pro Ala Trp Asn Lys Gln Arg
20 25 30

Gly Ser Ser Met Pro Val Asn Arg Tyr Met Pro Phe Glu Val Glu Val
35 40 45

Glu Asp Ile Ser Leu Pro Asp Arg Thr Trp Pro Asp Lys Lys Ile Thr
50 55 60

Val Ala Pro Gln Trp Cys Ala Val Asp Leu Arg Asp Gly Asn Gln Ala
65 70 75 80

Leu Ile Asp Pro Met Ser Pro Glu Arg Lys Arg Arg Met Phe Glu Leu
85 90 95

Leu Val Gln Met Gly Phe Lys Glu Ile Glu Val Gly Phe Pro Ser Ala
100 105 110

Ser Gln Thr Asp Phe Asp Phe Val Arg Glu Ile Ile Glu Lys Gly Met
115 120 125

Ile Pro Asp Asp Val Thr Ile Gln Val Leu Val Gln Ala Arg Glu His
130 135 140

Leu Ile Arg Arg Thr Phe Glu Ala Cys Glu Gly Ala Lys Asn Val Ile
145 150 155 160

Val His Phe Tyr Asn Ser Thr Ser Ile Leu Gln Arg Asn Val Val Phe
165 170 175

Arg Met Asp Lys Val Gln Val Lys Lys Leu Ala Thr Asp Ala Ala Glu
180 185 190

Leu Ile Lys Thr Ile Ala Gln Asp Tyr Pro Asp Thr Asn Trp Arg Trp
195 200 205

Gln Tyr Ser Pro Glu Ser Phe Thr Gly Thr Glu Val Glu Tyr Ala Lys

```
    210                 215                 220

Glu Val Val Asp Ala Val Val Glu Val Met Asp Pro Thr Pro Glu Asn
225                 230                 235                 240

Pro Met Ile Ile Asn Leu Cys Ser Thr Val Glu Met Ile Thr Pro Asn
                245                 250                 255

Val Tyr Ala Asp Ser Ile Glu Trp Met His Arg Asn Leu Asn Arg Arg
            260                 265                 270

Asp Ser Ile Ile Leu Ser Leu His Pro His Asn Asp Arg Gly Thr Gly
        275                 280                 285

Val Gly Ala Ala Glu Leu Gly Tyr Met Ala Gly Ala Asp Arg Ile Glu
    290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                325                 330                 335

Phe Thr Asp Ile Arg Gln Ile Arg Ser Thr Val Glu Tyr Cys Asn Gln
            340                 345                 350

Leu Arg Val Pro Glu Arg His Pro Tyr Gly Gly Asp Leu Val Phe Thr
        355                 360                 365

Ala Phe Ser Gly Ser His Gln Asp Ala Val Asn Lys Gly Leu Asp Ala
    370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
                405                 410                 415

Pro Lys Asp Val Gly Arg Asp Tyr Glu Ala Val Ile Arg Val Asn Ser
            420                 425                 430

Gln Ser Gly Lys Gly Gly Val Ala Tyr Ile Met Lys Thr Asp His Gly
        435                 440                 445

Leu Gln Ile Pro Arg Ser Met Gln Val Glu Phe Ser Thr Val Val Gln
    450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
            500                 505                 510

Ile Thr Ala Glu Leu Ile His Asn Gly Lys Asp Val Thr Val Asp Gly
        515                 520                 525

Arg Gly Asn Gly Pro Leu Ala Ala Tyr Ala Asn Ala Leu Glu Lys Leu
    530                 535                 540

Gly Ile Asp Val Glu Ile Gln Glu Tyr Asn Gln His Ala His Thr Ser
545                 550                 555                 560

Asp Asp Asp Ala Glu Ala Ala Ala Tyr Val Leu Ala Glu Val Asn Gly
                565                 570                 575

Arg Lys Val Trp Gly Val Gly Ile Ala Gly Ser Ile Thr Tyr Ala Ser
            580                 585                 590

Leu Lys Ala Val Thr Ser Ala Val Asn Arg Ala Leu Asp Val Asn His
        595                 600                 605

Glu Ala Val Leu Ala Gly Gly Val
    610                 615
```

<210> SEQ ID NO 63

-continued

<211> LENGTH: 1851
<212> TYPE: DNA
<213> ORGANISM: Artificial Sequence
<220> FEATURE:
<223> OTHER INFORMATION: leuA_P247C+R558H+G561D_nt

<400> SEQUENCE: 63

```
atgtctccta acgatgcatt catctccgca cctgccaaga tcgaaacccc agttgggcct      60

cgcaacgaag gccagccagc atggaataag cagcgtggct cctcaatgcc agttaaccgc     120

tacatgcctt tcgaggttga ggtagaagat atttctctgc cggaccgcac ttggccagat     180

aaaaaaatca ccgttgcacc tcagtggtgt gctgttgacc tgcgtgacgg caaccaggct     240

ctgattgatc cgatgtctcc tgagcgtaag cgccgcatgt ttgagctgct ggttcagatg     300

ggcttcaaag aaatcgaggt cggtttccct tcagcttccc agactgattt tgatttcgtt     360

cgtgagatca tcgaaaaggg catgatccct gacgatgtca ccattcaggt tctggttcag     420

gctcgtgagc acctgattcg ccgtactttt gaagcttgcg aaggcgcaaa aaacgttatc     480

gtgcacttct acaactccac ctccatcctg cagcgcaacg tggtgttccg catggacaag     540

gtgcaggtga agaagctggc taccgatgcc gctgaactaa tcaagaccat cgctcaggat     600

tacccagaca ccaactggcg ctggcagtac tcccctgagt ccttcaccgg cactgaggtt     660

gagtacgcca aggaagttgt ggacgcagtt gttgaggtca tggatccaac tcctgagaac     720

ccaatgatca tcaacctgtg ttccaccgtt gagatgatca cccctaacgt ttacgcagac     780

tccattgaat ggatgcaccg caatctaaac cgtcgtgatt ccattatcct gtccctgcac     840

ccgcacaatg accgtggcac cggcgttggc gcagctgagc tgggctacat ggctggcgct     900

gaccgcatcg aaggctgcct gttcggcaac ggcgagcgca ccggcaacgt ctgcctggtc     960

accctggcac tgaacatgct gacccagggc gttgaccctc agctggactt caccgatata    1020

cgccagatcc gcagcaccgt tgaatactgc aaccagctgc gcgttcctga gcgccaccca    1080

tacggcggtg acctggtctt caccgctttc tccggttccc accaggacgc tgtgaacaag    1140

ggtctggacg ccatggctgc caaggttcag ccaggtgcta gctccactga agtttcttgg    1200

gagcagctgc gcgacaccga atgggaggtt ccttacctgc ctatcgatcc aaaggatgtc    1260

ggtcgcgact acgaggctgt tatccgcgtg aactcccagt ccggcaaggg cggcgttgct    1320

tacatcatga agaccgatca cggtctgcag atccctcgct ccatgcaggt tgagttctcc    1380

accgttgtcc agaacgtcac cgacgctgag ggcggcgagg tcaactccaa ggcaatgtgg    1440

gatatcttcg ccaccgagta cctggagcgc accgcaccag ttgagcagat cgcgctgcgc    1500

gtcgagaacg ctcagaccga aaacgaggat gcatccatca ccgccgagct catccacaac    1560

ggcaaggacg tcaccgtcga tggccgcggc aacggcccac tggccgctta cgccaacgcg    1620

ctggagaagc tgggcatcga cgttgagatc caggaataca accagcacgc ccacacctcg    1680

gatgacgatg cagaagcagc cgcctacgtg ctggctgagg tcaacggccg caaggtctgg    1740

ggcgtcggca tcgctggctc catcacctac gcttcgctga aggcagtgac ctccgccgta    1800

aaccgcgcgc tggacgtcaa ccacgaggca gtcctggctg gcggcgttta a             1851
```